US010792395B2

(12) United States Patent
Mazza et al.

(10) Patent No.: US 10,792,395 B2
(45) Date of Patent: Oct. 6, 2020

(54) METHODS AND DEVICES FOR THE PRODUCTION OF DECELLULARISED TISSUE SCAFFOLDS

(71) Applicant: UCL Business Ltd, London, Greater London (GB)

(72) Inventors: Giuseppe Mazza, London (GB); Walid Al-Akkad Abu Zeina, London (GB); Massimo Pinzani, London (GB)

(73) Assignee: UCL Business Ltd, London, Greater London (GB)

( * ) Notice: Subject to any disclaimer, the term of this patent is extended or adjusted under 35 U.S.C. 154(b) by 166 days.

(21) Appl. No.: 15/748,390

(22) PCT Filed: Jul. 29, 2016

(86) PCT No.: PCT/GB2016/052349
§ 371 (c)(1),
(2) Date: Jan. 29, 2018

(87) PCT Pub. No.: WO2017/017474
PCT Pub. Date: Feb. 2, 2017

(65) Prior Publication Data
US 2018/0214609 A1 Aug. 2, 2018

(30) Foreign Application Priority Data
Jul. 30, 2015 (GB) .................................. 1513461.2

(51) Int. Cl.
*A61L 27/36* (2006.01)
*C12M 1/33* (2006.01)
*C12N 5/071* (2010.01)
*B01L 3/00* (2006.01)

(52) U.S. Cl.
CPC ........ *A61L 27/3691* (2013.01); *A61L 27/3633* (2013.01); *B01L 3/5027* (2013.01); *B01L 3/502707* (2013.01); *C12M 1/33* (2013.01); *C12M 45/02* (2013.01); *C12N 5/067* (2013.01); *C12N 5/0671* (2013.01); *C12N 5/0676* (2013.01); *C12N 5/0679* (2013.01); *A61L 2430/40* (2013.01); *B01L 2300/0864* (2013.01); *B01L 2300/0867* (2013.01); *B01L 2400/0487* (2013.01); *C12N 2527/00* (2013.01)

(58) Field of Classification Search
CPC ............. A61L 27/3691; A61L 27/3633; A61L 2430/40; C12N 5/0671; C12N 5/067; C12N 5/0676; C12N 5/0679; C12N 2527/00; B01L 3/5027; B01L 2300/0864; B01L 2300/0867; B01L 2400/0487; B01L 3/502707; C12M 1/33; C12M 45/02
See application file for complete search history.

(56) References Cited

U.S. PATENT DOCUMENTS 6,753,181 B2 6/2004 Atala
2005/0249816 A1 11/2005 Atala et al.

OTHER PUBLICATIONS

Wolf M.T. et al., "A Hydrogel Derived From Decellularized Dermal Extracellular Matrix", Biomaterials, 2012, vol. 33, No. 29, pp. 7028-7038. attached—Author Manuscript pp. 1-23. (Year: 2012).*
Pellegata A.F. et al., "A novel device for the automatic decellularization of biological tissues", Int. J Artif. Organs, 2012, vol. 35, No. 3, pp. 191-198. (Year: 2012).*
Crapo, et al., "An overview of tissue and whole organ decellularization processes", Biomaterials, 32(12): 3233-3243 (2011).
Wang, et al., "Decellularization technology in CNS tissue repair", Exper Rev. Neurother. 15(5): 493-500 (2015).
Reing, et al., "The Effects of Processing Methods upon Mechanical and Biologic Properties of Porcine Dermal Extracellular Matrix Scaffolds", Biomaterials, 31(33): 8626-8633 (2010).
Faulk, et al., "Decellularization and Cell Seeding of Whole Liver Biologic Scaffolds Composed of Extracellular Matrix", Journal of Clinical and Experimental Hepatology, vol. 5, No. 1: 69-80 (2015).
Mazza, et al., "Decellularized human liver as a natural 3D-scaffold for liver bioengineering and transplantation", Scientific Reports, vol. 5, p. 13079 (2015).
PCT International Search Report and Written Opinion for International Application No. PCT/GB2016/052349 dated Nov. 23, 2016.

* cited by examiner

*Primary Examiner* — Satyendra K Singh
(74) *Attorney, Agent, or Firm* — Greenberg Traurig, LLP; Fang Xie

(57) ABSTRACT

This invention relates to a method of producing a decellularised tissue scaffold which comprising treating a sample of tissue with an osmotic reagent and a detergent whilst subjecting the tissue sample to oscillation with a displacement of 1 mm or more and a frequency of 3 Hz or more during these treatment steps. This method may be useful in producing acellular scaffolds that maintain the 3-D architecture and extracellular matrix composition and morphology of the native tissue.

32 Claims, 12 Drawing Sheets

METHODS AND DEVICES FOR THE PRODUCTION OF DECELLULARISED TISSUE SCAFFOLDS

CROSS-REFERENCE TO RELATED APPLICATIONS

This application is a National Phase Application under 35 U.S.C. § 371 of International Application No. PCT/GB2016/052349 filed Jul. 29, 2016, which claims the benefit of and priority to GB Application No. 1513461.2 filed Jul. 30, 2017, the contents of both of which applications are incorporated by reference herein in their entireties.

This invention relates to the production of extracellular matrix (ECM) scaffolds, for example for use in therapy, disease modelling, drug screening, diagnosis, and discovery of biomarkers.

Tissue engineering is an emerging field aimed at improving the quality of life for millions of people worldwide by restoring organ function and providing 3D-platforms for studying human disease ex vivo. A key challenge in tissue engineering is the development of 3D-structures ("scaffolds") that recapitulate the physiological architecture and composition of tissues and organs.

2-D cell cultures and animal models are commonly used as pre-clinical models for studying human diseases. Although useful information has been obtained from these models, both systems are characterised by several limitations, including: early cellular dedifferentiation and early senescence when in culture, lack of bidirectional tumour-stromal crosstalk, impaired gene and protein expression, lack of correlation with human biology and species-specific toxicity.

Biological scaffolds composed of extracellular matrix (ECM) are produced by decellularisation of samples of tissue. ECM integrity, bioactivity and 3-D organisation may be preserved in the decellularised scaffolds. However, the production of biological scaffolds is challenging due to the lack of pedicles/vessels that can be cannulated to allow perfusion-decellularisation. Reported protocols are characterised by low speed agitation and require prolonged (e.g. weeks) exposure of the tissue to decellularisation reagents. Furthermore, these protocols are not efficient for complete decellularisation of small-scale tissues and the exterior surface of the tissue is often damaged by the continuous exposure to detergents and enzymes.

The present inventors have recognised that a range of different types of tissues may be decellularised without damaging the extracellular matrix using treatment regimens that are characterized by one or more cycles of treatment with sets of different cell damaging agents under high frequency oscillation. These regimes may be useful in the reproducible production of acellular scaffolds that maintain the 3-D architecture and extracellular matrix composition and morphology of the native tissue.

An aspect of the invention provides a method of producing a decellularised tissue scaffold comprising;
  (i) providing a sample of tissue,
  (ii) treating the sample with an osmotic reagent, and
  (iii) treating the sample with a detergent,
  wherein the tissue sample is subjected to oscillation with a displacement of 1 mm or more and a frequency of 3 Hz or more during steps (ii) and (iii),
  thereby producing a decellularised tissue scaffold.

A decellularised tissue scaffold produced by the claimed methods consists of acellular extracellular matrix (ECM) from the source tissue and retains the three dimensional architecture, ECM composition and bioactivity of the ECM of the source tissue.

A decellularised tissue scaffold may be produced using the methods described herein in less than 6 hours, less than 3 hours, or less than 2 hours.

During treatment with the osmotic reagent, detergent and other decellularisation reagents, the tissue sample is subjected to high frequency oscillation i.e. oscillation of 3 Hz or more. This oscillation enhances the distribution of reagents within the tissue, increases the efficiency of cell lysis and/or improves the flushing of cellular or immunogenic components from the tissue. This reduces the time needed for complete decellularisation, while preserving ECM proteins, 3D-histoarchitecture and the ability of the ECM to induce homing, differentiation and proliferation of cells.

The oscillation may be in a single plane, preferably in a single linear dimension or line. Any direction or plane of oscillation may be employed. For example, the oscillation may be horizontal (i.e. perpendicular to gravitational force) or vertical (i.e. parallel to gravitational force).

The sample may be oscillated at a frequency of 3 Hz or more, 5 Hz or more or 10 Hz or more and up to 100 Hz, up to 75 Hz, up to 50 Hz or up to 30 Hz. Suitable ranges of oscillation frequency include any one of the listed lower limits in combination with any of the listed upper limits. For example, the sample may be oscillated at 3 to 75 Hz, for example 10 to 50 Hz.

The oscillation may subject the sample to a g-force of 4 to 500 $ms^{-2}$, preferably 40 to 50 $ms^{-2}$, for example 42 $ms^{-2}$ to 47 $ms^{-2}$. For example, oscillation in any direction may be performed at 1.8 $ms^{-2}$ to 181.1 $ms^{-2}$, preferably about 45.3 $ms^{-2}$.

The displacement of the oscillations may be 1 mm or more, 5 mm or more, 7.5 mm or more, or 10 mm or more, and up to 50 mm, up to 30 mm or up to 25 mmm. Suitable ranges of displacement may include any one of the listed lower limits in combination with any of the listed upper limits. For example, the sample may be oscillated with a displacement of 5 to 50 mm, preferably 7.5 to 25 mm.

Suitable oscillating motors and other apparatus for oscillating tissue samples are well-known in the art. Suitable means include oscillatory tissue disruptors. For example, tissue samples may be oscillated in a vertical direction using a TissueLyser LT™ device (Qiagen NV, NL) or a horizontal direction using a TissueLyser II™ device (Qiagen, NV, NL).

Samples of tissue suitable for decellularisation as described herein include sections or blocks of length, width or diameter of 0.1-4 cm, for example 0.2-1.0 cm (e.g. a section with a volume of 0.005 $cm^3$ to 10 $cm^3$, for example 0.008 $cm^3$ to 1 $cm^3$, for example about 0.125 $cm^3$). The section or block may be of any shape. Preferably, the section is of a suitable size for manipulation in standard laboratory vessels, such as multi-well plates, and may be, for example, approximately cubic with sides of about 0.5 cm.

Small non-vascularized sections or wedges may be useful in reproducing the complexity of 3D tissue microenvironment in small scale for disease modelling and drug screening. Suitable samples may be obtained by punch biopsy, needle biopsy, scalpel cleavage, or using an automatic or non-automatic dicer machine.

Suitable tissue samples include kidney, muscle, bone, adipose, cartilage, lung, bladder, cornea, skin, liver, intestine, pancreas, prostate, breast, spleen, placenta and heart samples. In some embodiments, the tissue sample may include combination of different tissues, such as an animal tail.

The tissue sample may be mammalian tissue, for example pig, sheep, rodent, non-human primate or human tissue. Preferably, the tissue sample is human tissue.

Human tissue for decellularisation may be obtained from human organs that are unsuitable for clinical use in transplantation. Suitable organs may be obtained in accordance with relevant national laws and ethical guidelines. In addition to this, human tissue may be obtained from tissue resection after surgery.

In some embodiments, the sampled tissue may be normal tissue which does not display pathology associated with damage or disease.

In other embodiments, the sampled tissue may be pathological tissue which displays pathology associated with damage or disease. For example, sampled tissue may be fatty, fibrotic, cancerous, inflamed or display one or more other features associated with disease or damage. In some embodiments, pathological tissue may display pathology associated with acute or chronic disease, including viral infections, alcohol or toxin damage, fibrosis, amyloidosis and cancer. Examples of pathological tissue include fibrotic, cirrhotic or cancerous liver tissue (from different etiologies), amyloidotic kidney tissue, amyloidotic heart tissue, fibrotic intestine tissue, for example from a patient with Crohn's disease, ulcerative colitis or Inflammatory Bowel Disease (IBD), cancerous pancreatic tissue, fibrotic lung tissue and cancerous breast tissue.

Decellularised scaffolds produced from pathological tissue samples may have a different structure and composition from scaffolds produced from healthy tissue samples. For example, the morphology of the pathological scaffold or the amounts or relative amounts of ECM components, such as collagen, tenascin and laminin, may be altered in scaffolds from pathological tissue samples compared to healthy tissue samples. Characteristic features of a disease (e.g. amyloidogenic protein) may be associated with the ECM and may be retained during decellularisation, thereby increasing the sensitivity of diagnosis. This may be useful in obtaining specific disease-modified scaffolds for disease modelling, drug screening and diagnosis.

Pathological tissue may be obtained from an individual with a disease.

Methods of obtaining and storing tissue and tissue samples for decellularisation as described herein are well-known in the art. For example, the tissue may be heparinized to prevent coagulation and/or perfused with cryoprotectant agents. Suitable cryoprotectants include DMSO, ethylene glycol, propylene glycol, glycerol, 2-methyl-2,4 pentanediol (MPD), and sucrose.

The tissue sample is decellularised by a series of sequential exposures to decellularisation reagents, which include osmotic reagents, detergents and optionally proteases and other enzymes, whilst undergoing oscillation. The combination of oscillation and sequential exposure to decellularisation reagents detaches cells and cell debris from the extracellular matrix (ECM) of the tissue sample and removes them without damaging the ECM.

The tissue sample may be exposed to a decellularisation reagent by immersing the tissue in the reagent. The immersed sample is then oscillated.

The tissue sample may be oscillated continuously throughout the decellularisation or the oscillation may be stopped to allow removal of the previous decellularisation reagent and addition of the new decellularisation reagent.

Each step of exposing the tissue sample to a decellularisation reagent may comprise one or more separate treatments with the decellularisation reagent. For example, step (ii) may comprise one, two, three or more separate treatments with an osmotic reagent. Step (iii) may comprise one, two, three or more separate treatments with a detergent.

The order of exposure to the different decellularisation reagents is based on their different mechanism of actions. Optionally, the cells in the sample may initially be mechanically damaged to promote an intense cellular disruption. The exposure to hypotonic solutions (step ii) amplifies the cell lysis, while washing out cellular materials. The exposure to tissue is exposed to detergent (step iii) to effectively wash out cellular materials.

A method may comprise repeating step (ii) and/or step (iii) one or more times. For example, the tissue sample may be exposed to multiple cycles of treatment with decellularisation reagents. For example, the tissue sample may be subjected to multiple treatment cycles comprising steps (ii) and (iii) e.g. the tissue sample may be subjected to at least 2, at least 3 or at least 4 treatment cycles comprising steps (ii) and (iii).

Osmotic stress causes lysis of the cells in the tissue sample and amplifies the effects of the mechanical damage. Osmotic stress may be induced by exposing the tissue sample to one or more osmotic reagents which have a different osmotic pressure to the cells in the tissue (i.e. a non-isotonic reagent). The tissue may be exposed to one or more hypotonic reagents which have a lower osmotic pressure than the cells and subject the cells to a hypotonic environment and/or one or more hypertonic reagents which have a higher osmotic pressure than cells and subjects the cells to a hypertonic environment. Hypotonic reagents may be preferred in some embodiments.

Hypertonic reagents may be useful, for example, in dissociating DNA from proteins. Suitable hypertonic reagents are well-known in the art and include water, saline (e.g. >0.9% (w/v) NaCl, for example 3% to 10% (w/v) NaCl), which may optionally be buffered for example with phosphate, borate or Tris, polyethylene glycol and dextrose solutions.

In some preferred embodiments, the osmotic agent is saline, for example 8.7% (w/v) NaCl.

Hypotonic reagents may be useful for example in inducing cell lysis through simple osmotic effects, with minimal changes in the molecules and architecture of the ECM. Suitable hypotonic reagents are well-known in the art and include deionised water and saline of <0.9% (w/v) NaCl.

In some preferred embodiments, the osmotic agent is deionised water.

Detergents solubilise lipids and fats in the tissue and facilitate the removal of cellular debris from the ECM.

Preferred detergents may include anionic detergents, such as BigCHAP, Bis (polyethylene glycol bis[imidazoyl carbonyl]), Brij®, Brij® 35, Brij® 56, Brij® 72, Brij® 76, Brij® 92V, Brij® 97, Brij® 58P, Cremophor® EL (Sigma, Aldrich), N-Decanoyl- N-methylglucamine, n-Decyl a-D-glucopyranoside, Decyl b-D-maltopyranoside, n-Dodecyl a-D-maltoside, Heptaethylene glycol monodecyl ether, n-Hexadecyl b-D-maltoside, Hexaethylene glycol monododecyl ether, Hexaethylene glycol monohexadecyl ether, Hexaethylene glycol monooctadecyl ether, Hexaethylene glycol monotetradecyl ether, Igepal CA-630, Methyl-6-O-(N-heptylcarbamoyl)-a-D-glucopyranoside, Nonaethylene glycol monododecyl ether, N-Nonanoyl-N-methylglucamine, Octaethylene glycol monodecyl ether, Octaethylene glycol monododecyl ether, Octaethylene glycolmonooctadecyl ether, Octaethylene glycol monotetradecyl ether, Octyl-b-D-glucopyranoside, Pentaethylene glycol monodecyl ether, Pentaethylene glycol monohexadecyl ether, Pentaethylene glycol monohexyl ether, Pentaethylene glycol monooctadecyl ether, Pentaethylene glycolmonooctyl ether, Polyethylene glycol ether, Polyoxyethylene, Saponin, Span® 20, Span® 40, Span® 60, Span® 65, Span® 80, Span® 85 (Sigma Aldrich), Tergitol, Tetradecyl-b-D-maltoside, Tetraethylene glycol monodecyl ether, Tetraethylene glycol monododecyl ether, Tetraethylene glycol monomonotetradecyl ether, Triton® CF-21, Triton® CF-32, Triton® DF-12, Triton® DF-16, Triton® GR-5M, Triton X®-100, Triton X®-102, Triton X®-15, Triton X®-151, Triton X®-207, Triton®, TWEEN® (Sigma Aldrich), Tyloxapol, n-Undecyl b-D-glucopyranoside, and combinations thereof. Any zwitterionic detergent will work for purposes of the present invention. Preferred zwitterionic detergents include, but are not limited to the following: CHAPS, CHAPSO, Sulfobetaine 3-10 (SB 3-10), Sulfobetaine 3-12 (SB 3-12), Sulfobetaine 3-14 (SB 3-14), ASB-14, ASB-16, ASP-C80, Non-Detergent Sulfobetaine (ND SB) 201, DDMAB, DDMAU, EMPIGEN BB®Detergent, 30% Solution, Lauryldimethylamine Oxide (LDAO) 30% solution, ZWITTERGENT® 3-08 Detergent, ZWITTERGENT® 3-10 Detergent, ZWITTERGENT® 3-12 Detergent, ZWITTERGENT® 3-14 Detergent, ZWITTERGENT® 3-16 Detergent, and combinations thereof.

Preferred anionic detergents include sodium dodecyl phosphate (SDS) and sodium deoxycholate (SdC). For example, the tissue sample may be exposed to 0.01 to 5% SDS, for example 0.01-1% SDS and/or 0.1 to 10% sodium deoxycholate (SdC), for example about 4% sodium deoxycholate. In some preferred embodiments, the detergent may comprise 4% SDS.

Detergents may include non-ionic detergents, such as chenodeoxycholic acid, chenodeoxycholic acid sodium salt, cholic acid, ox or sheep bile, dehydrocholic acid, deoxycholic acid, deoxycholic acid methyl ester, digitonin, digitoxigenin, N,N-dimethyldodecylamine N-oxide, docusate sodium salt, glycochenodeoxycholic acid sodium salt, glycocholic acid hydrate, glycocholic acid sodium salt hydrate, glycocholic acid sodium salt, glycolithocholic acid 3-sulfate disodium salt, glycolithocholic acid ethyl ester, N-laurolysarcosine sodium salt, N-laurolysarcosine salt solution, lithium dodecyl sulfate, Lugol solution, niaproof 4, Triton®, Triton® QS-15, Triton® QS-44 solution, 1-octanesulfonic acid sodium salt, sodium 1-butanesulfonate, sodium 1-deccanesulfonate, sodium 1-dodecanesulfonate, sodium 1-heptanesulfonate anhydrous, sodium 1-nonanesulfonate, sodium 1-propanesulfonate monohydrate, sodium 2-bromoethanesulfonate, sodium choleate hydrate, sodium choleate, sodium deoxycholate, sodium deoxycholate monohydrate, sodium dodecyl sulfate, sodium hexanesulfonate anhydrous, sodium octyl sulfate, sodium pentanesulfonate anhydrous, sodium taurocholate, taurochenodeoxycholic acid sodium salt, taurochenodeoxycholic acid sodium salt monohydrate, taurochenodeoxycholic acid sodium salt hydrate, taurolithocholic acid 3-sulfate disodium salt, tauroursodeoxycholic acid sodium salt, Triton X®-200, Triton X®GS-20 solution, trizma dodecyl sulfate, ursodeoxycholic acid, and combinations thereof.

Preferred non-ionic detergents include polyethylene glycol and Triton™ X-100, e.g. polyethylene glycol p-(1,1,3, 3-tetramethylbutyl)-phenyl ether (also called polyoxyethylene octyl phenyl ether or TX-100; CAS 9002-93-1; $C_{14}H_{22}O(C_2H_4O)_n$, (n=9-10)). For example, the tissue sample may be exposed to 0.01 to 10% TX-100, or 1 to 3% TX-100, for example 3% TX-100.

Detergents may include zwitterionic detergents, such as CHAPS (3-[(3-Cholamidopropyl)dimethylammonio]-1-propanesulfonate), sulfobetaine-10 (3-(Decyldimethylammonio)propanesulfonate), sulfobetaine-16 (n-Hexadecyl-N, N-dimethyl-3-ammonio-1-propanesulfonate), and Tri(n-butyl)phosphate. For example, the tissue sample may be exposed to 0.01 to 5% zwitterionic detergent, for example 0.01-1% zwitterionic detergent.

Numerous other suitable detergents are known in the art and available from commercial sources (e.g. Sigma Aldrich Co LLC, MO, USA).

The tissue may be exposed to two or more different detergents. For example, step (iii) may comprise exposing the tissue sample to an anionic detergent, such as SDS and/or SdC and a non-ionic detergent, such as TX-100.

In some embodiments, the sample may be exposed to SDS, SdC and TX-100, for example 3% SDC; 0.5% SDS and 3% TX-100.

In some embodiments, the tissue sample may be exposed to a detergent in solution with a chelating agent, such as EDTA or EGTA, which chelate divalent metallic ions, such as $Ca^{2+}$, and disrupts cell adhesion to the ECM.

In some embodiments, the tissue sample may be exposed to an alcohol. The alcohol used can be any alcohol, and preferred alcohols are selected from, but are not limited to, the following group: ethyl alcohol, methyl alcohol, n-propyl alcohol, iso-propyl alcohol, n-butyl alcohol, sec-butyl alcohol, t-butyl alcohol, iso-amyl alcohol, n-decyl alcohol and combinations thereof.

In some embodiments, a method of decellularisation may further comprise treating the tissue sample with protease and/or nuclease, for example endonuclease or exonuclease. Preferably, the tissue sample is treated with protease.

The sample may be treated with protease in a single step or as part of a repeated cycle of treatment with decellularisation agents.

Proteases degrade proteins in the tissue sample, disrupt cellular and sub-cellular structures and break cell linkages with the ECM. Suitable proteases are well-known in the art and include dispase and trypsin. The tissue sample may be exposed to 0.0025-0.25% (w/v) trypsin, for example 0.025% trypsin.

In some embodiments, the tissue sample may be exposed to a protease in solution with a chelating agent, such as EDTA, which chelates divalent metallic ions, such as $Ca^{2+}$, and disrupts cell adhesion to the ECM.

In preferred embodiments, the tissue sample may be treated with protease and detergent simultaneously.

For example, the sample may be treated with a solution comprising SDS, SdC, TX-100 and/or Trypsin. These components may be used in any combination or concentration, for example 0.1-10% SdC; 0.1-10% SDS; 0.1-20% TX-100; 0.05-0.5% Trypsin-EDTA, 0.1-10% NaCl, such as 3% SdC; 0.5% SDS; 3% TX-100; 0.025% Trypsin-EDTA, 4.3% NaCl.

In some embodiments, a method of decellularisation may further comprise treating the tissue sample with peracetic acid (PAA), which denatures DNA and/or ammonium hydroxide, which breaks phosphodiester bonds.

The tissue sample may be washed following treatment with a decellularisation reagent, for example between one or more of the above steps and/or between cycles.

The tissue sample may washed with a suitable wash solution, for example a buffered saline, such as phosphate buffered saline (PBS), 0.1-10% saline solution or deionised water. For example, the sample may be washed with 1% PBS after exposure to detergent and optionally protease and/or after exposure to osmotic agent.

Typically, the tissue sample is washed with 1% PBS for 1 min at ambient temperature.

In some embodiments, a wash step may comprise two or more sequential exposures to PBS.

Before steps (ii) and (iii), the cells in the tissue sample may be subjected to mechanical damage to facilitate their removal. The cells may be mechanically damaged by any suitable technique that damages the cells of the tissue without affecting the extracellular matrix, including freeze/thaw, sonication, or high intensity focussed ultrasound (HIFU).

Preferably, the tissue sample is subjected to at least one cycle of freeze/thaw before decellularisation.

In some embodiments, mechanical damaging techniques may not be repeated after the initial treatment. For example, such as freeze/thaw treatment after exposure to other decellularisation reagents may lead to ECM damage.

In other embodiments, the cells in the tissue sample may be subjected to mechanical damaging one or more times after the initial treatment e.g. after one or more repetitions of steps (ii) and/or (iii). For example, the tissue sample may be subjected to HIFU or sonication one or more times.

Preferably, the cells are mechanically damaged by subjecting the tissue sample to one or more freeze/thaw cycles. For example, the tissue may be frozen at −20° C. or less, preferably −50° C. or less, −60° C. or less, −70° C. or less, and then thawed one or more times. Frozen tissue may be conveniently thawed at 4° C. to 37° C. In some embodiments, the tissue may be thawed at about 4° C. to minimise temperature gradients within the tissue that may damage the ECM. For example, the tissue may be frozen at about −80° C. for 24 hours or more and then thawed at about 4° C. In some preferred embodiments, the tissue sample may be thawed at 37° C., for example for 45 minutes to 1 hour, and then immersed in PBS at 37° C., for example for 15 minutes.

Tissue samples that are subjected to freeze/thaw are preferably dry to prevent ECM damage. In some embodiments, a tissue sample may be dried before the freeze/thaw step, for example by 5 to 30 minutes exposure at room temperature.

The tissue sample may be subjected to freeze/thaw in an isotonic buffer, for example saline, such as 0.90% (w/v) NaCl, or PBS.

The mechanical damage promotes intense cellular disruption within the tissue. The cell lysis caused by the mechanical damage may be amplified by treatment with the osmotic reagent and detergent in steps (ii) and (iii).

In some embodiments of a first set of embodiments, steps (ii) and (iii) may comprise;
(a) exposing the sample to deionised water, e.g. for 2 minutes, and
(b) repeating step (a) 0-50 times (e.g. until supernatant is clear)
(c) exposing the sample to detergent and protease, e.g. for 2 minutes,
(d) exposing the sample to detergent and protease, e.g. for 4 minutes,
(e) repeating step (d),
(f) exposing the sample to saline, e.g. for 2 minutes,
(g) repeating step (f) 0-10 times until tissue is clean of any reagents and protease
(h) repeating steps (a) to (e) 0-10 times (e.g. until tissue is completely white),
(i) exposing the sample to saline, e.g. for 5 minutes,
(j) repeating step (i) 0-10 times.

In other embodiments of the first set, steps (ii) and (iii) may comprise; may comprise;
(a) exposing the sample to deionised water, e.g. for 2 minutes, and
(b) repeating step (a) 4 times,
(c) exposing the sample to detergent and protease, e.g. for 2 minutes,
(d) exposing the sample to detergent and protease, e.g. for 4 minutes,
(e) repeating step (d),
(f) exposing the sample to saline, e.g. for 2 minutes,
(g) repeating step (f) 4 times,
(h) repeating steps (a) to (e).
(i) exposing the sample to saline, for example PBS, e.g. for 5 minutes,
(j) repeating step (i) 2 times.

Suitable tissue samples include liver, for example human liver, or intestine, for example human intestine.

A suitable regimen is shown in Table 2 (HL3 and HI5).

In other embodiments of the first set, steps (ii) and (iii) may comprise;
(a) exposing the sample to deionised water, e.g. for 2 minutes
(b) repeating step (a) 10 times
(c) exposing the sample to detergent and protease, e.g. for 2 minutes,
(d) exposing the sample to detergent and protease, e.g. for 4 minutes
(e) repeating step (d)
(f) exposing the sample to saline, e.g. for 2 minutes;
(g) repeating step (f) 4 times
(h) repeating steps (a) to (e).
(i) exposing the sample to saline, for example PBS, e.g. for 5 minutes,
(j) repeating step (i) 2 times Suitable tissue samples include liver, for example human liver.

A suitable regimen is shown in Table 2 (HL43).

In other embodiments of the first set, steps (ii) and (iii) may comprise;
(a) exposing the sample to deionised water, e.g. for 2 minutes,
(b) repeating step (d) 11 times,
(c) exposing the sample to detergent and protease, e.g. for 2 minutes,
(d) exposing the sample to detergent and protease, e.g. for 4 minutes,
(e) repeating step (d),
(f) exposing the sample to saline, e.g. for 2 minutes
(g) exposing the sample to saline, for example PBS, e.g. for 5 minutes,
(h) repeating step (g) 2 times;

Suitable tissue samples include liver, for example human liver.

A suitable regimen is shown in Table 2 (HL36).

In other embodiments of the first set, steps (ii) and (iii) may comprise;
(a) exposing the sample to deionised water, e.g. for 2 minutes
(b) repeating step (a) 5 to 10 times
(c) exposing the sample to detergent, e.g. for 2 minutes,
(d) repeating step (a) 5 to 10 times,
(e) exposing the sample to saline, for example PBS,
(f) optionally repeating steps (a) to (e) one or more times.

Suitable tissue samples include kidney, for example human kidney, or heart, for example human heart.

The sample may be washed between said steps using PBS.

A suitable regimen is shown in Table 2.

In the first set of embodiments, the tissue sample may be oscillated vertically at 50 Hz, for example using a TissueLyser LT™.

In some embodiments of a second set of embodiments, steps (ii) and (iii) may comprise;
(a) exposing the sample to deionised water, e.g. for 2 minutes,
(b) repeating step (a) 19 times,
(c) exposing the sample to detergent and protease for 2 minutes,
(d) exposing the sample to detergent and protease, e.g. for 4 minutes
(e) repeating step (d),
(f) exposing the sample to saline, e.g. for 2 minutes;
(g) repeating step (f) 4 times.
(h) repeating steps (a) to (e) 2 times.
(i) exposing the sample to saline, for example PBS, e.g for 5 minutes,
(j) repeating step (i) 2 times A suitable regimen is shown in Table 2 (HL4).

In other embodiments of the second set, steps (ii) and (iii) may comprise;
(a) exposing the sample to deionised water, e.g. for 2 minutes, and
(b) repeating step (a) 9 times,
(c) exposing the sample to detergent and protease, e.g. for 2 minutes,
(d) exposing the sample to detergent and protease, e.g. for 4 minutes,
(e) repeating steps (d),
(f) repeating steps (c) to (e),
(g) exposing the sample to saline, for example PBS, e.g. for 5 minutes, and
(h) repeating step (g) 2 times.

A suitable regimen is shown in Table 2 (HL43).

In other embodiments of the second set, steps (ii) and (iii) may comprise;
(a) exposing the sample to deionised water, e.g. for 2 minutes,
(b) repeating step (a) 9 times,
(c) exposing the sample to detergent and protease, e.g. for 2 minutes,
(d) exposing the sample to detergent and protease, e.g. for 4 minutes, and
(e) repeating step (d),
(f) exposing the sample to saline for example PBS, e.g. for 5 minutes, and
(g) repeating step (f) 2 times.

A suitable regimen is shown in Table 2 (HL36).

In other embodiments of the second set, steps (ii) and (iii) may comprise;
(a) exposing the sample to deionised water, e.g. for 2 minutes and
(b) repeating step (a) 19 times,
(c) exposing the sample to detergent and protease, e.g. for 2 minutes,
(d) exposing the sample to detergent and protease, e.g. for 4 minutes
(e) repeating step (d),
(f) exposing the sample to saline, e.g. for 2 minutes
(g) repeating step (f) 5 times,
(h) repeating steps (a) to (d) 5 times.
(i) exposing the sample to saline, for example PBS, e.g. for 5 minutes, and
(j) repeating step (i) 2 times A suitable regimen is shown in Table 2 (HL-C1).

In other embodiments of the second set, steps (ii) and (iii) may comprise;
(a) exposing the sample to deionised water, e.g. for 2 minutes and
(b) repeating step (a) 4 times,
(c) exposing the sample to detergent and protease, e.g. for 2 minutes,
(d) exposing the sample to detergent and protease, e.g. for 4 minutes
(e) repeating step (d)
(f) exposing the sample to peracetic acid (PAA) for 2 minutes
(g) repeating step (f) 1 times
(h) exposing the sample to Ammonium Hydroxide ($NH_4OH$) for 2 minutes
(i) repeating step (h) 2 times
(j) exposing the sample to deionised water, e.g. for 2 minutes and
(k) repeating step (j) 10 times.
(l) repeating steps (c) and (d),
(m) exposing the sample to saline, for example PBS, e.g. for 5 minutes,
(n) repeating step (m) 2 times A suitable regimen is shown in Table 2 (HP1).

In the second set of embodiments, the tissue sample may be oscillated horizontally at 30 Hz, for example using a TissueLyser II™.

Suitable saline solutions, detergent and protease solutions and other decellularisation reagents are described in more detail above.

Following decellularisation, the tissue sample may be sterilised, for example by exposure to a sterilising agent. Suitable sterilising agents include y-irradiation, electrolysed water and chemical agents, such as peracetic acid (PAA). The tissue sample may be exposed to 0.01% peracetic acid and 4% ethanol, for example for 30 minutes to 2 hours. For example, the decellularised tissue sample may be immersed in the sterilising agent and optionally subjected to oscillation, as described herein.

Following decellularisation and sterilisation, the decellularised tissue sample may be tested, for example for the absence of cells and/or the presence of ECM components, such as collagen, laminin, elastin, proteoglycans, hyaluronic acid, fibronectin, growth factors and extracellular proteases.

In case of amyloidotic tissue samples, the decellularised tissue sample may be tested, for amyloidotic fibrils.

Suitable techniques, including macroscopic visualisation, microscopy and immunohistochemical techniques, are well-known in the art.

Decellularised tissue sample, for example human tissue samples, may lack detectable myofilaments, endothelial cells, smooth muscle cells, and cell debris and nuclei in histologic sections using standard histological staining procedures.

Decellularised tissue samples produced as described herein preserve the 3-D organ morphology and architecture and the ECM bioactivity of the source tissue sample.

In some embodiments, the architecture and morphology of a decellularised tissue sample produced by the methods described above may be confirmed by electron microscopy.

Depending on the source tissue, the decellularised tissue sample may comprise a normal ECM or may be a disease modified ECM. For example, the decellularised tissue sample may comprise one or more structural alterations that are characteristic of a tissue disease or pathology.

The decellularised tissue samples allow effective attachment, migration, proliferation and three-dimensional organization of cells that are cultured in the scaffold. The decellularised tissue sample may also provide bioactive molecules and bioinductive properties, which maintain cell phenotype and functional properties, and encourage production of tissue specific matrix.

Following production of decellularised tissue sample as described herein, a method may comprise incubating the sample with a protease such as an elastase or matrix metalloproteinase (MMP). This may be useful in the identification of ECM related biomarkers.

Following production of decellularised tissue sample as described herein, a method may comprise subjecting the decellularised sample to proteomics analysis, for example using electrophoresis and/or mass spectrometry techniques. This may also be useful in the identification of ECM related biomarkers.

Following production of decellularised tissue scaffold as described herein, a method may comprise re-populating the decellularised scaffold with cells to produce an artificial tissue sample.

Suitable cells include healthy or diseased cells, such as human primary and cell line tissue cells (e.g. Tissue Sinusoidal Cells), endothelial cells, iPSCs or cells derived from patient-specific iPSCs, embryonic stem cells (hESCs), mesenchymal stem cells (hMSC), fetal stem cells (e.g. amniotic fluid stem cells), cancer cells, endothelial progenitor cells (EPC) and bipotent liver stem cells.

Decellularised liver samples may be repopulated with primary hepatocytes, hepatic stellate cells, or Kupffer cells. Decellularised intestine samples may be repopulated with epithelial cells, myofibroblast, endothelial cells, intestinal cancer cells, iPSCs or cells derived from patient-specific iPSCs, embryonic stem cells (hESCs), mesenchymal stem cells (hMSC) foetal stem cells (e.g. amniotic fluid stem cells) or bipotent liver stem cells. Decellularised pancreatic samples may be repopulated with Islet-beta cells, endothelial cells, pancreatic stellate cells, pancreatic cancer cells, iPSCs or cells derived from patient-specific iPSCs, embryonic stem cells (ESCs), mesenchymal stem cells (MSCs) or foetal stem cells (e.g. amniotic fluid stem cells). Decellularised kidney samples may be repopulated with podocytes, tubule cells, MSC, iPSC, foetal stem cells (e.g. amniotic fluid stem cells) or cancer cells. Decellularised heart samples may be repopulated with cardiomyocytes, endothelial cells, iPSC, foetal stem cells (e.g. amniotic fluid stem cells) or MSCs. Decellularised intestinal samples may be repopulated with intestinal stem cells, myofibroblasts, or Caco-2 cells.

The decellularised tissue sample may be repopulated by seeding the scaffold with cells into the scaffold and culturing under suitable conditions. For example, the cells may be directly injected into the parenchyma of the decellularised scaffold and/or dropped on the surface of the decellularised scaffold. The seeded scaffold may be cultured under static conditions, for example in a culture medium, or under dynamic conditions, for example in a bioreactor.

In some embodiments, the decellularised tissue scaffold may be repopulated with autologous human cells obtained from a patient, for example to produce artificial tissue for implantation into the patient. In other embodiments, the decellularised human scaffold may be repopulated with allogeneic human cells i.e. cells derived from a different human individual, for example to produce artificial tissue for implantation into the patient. In some embodiments, the allogeneic human cells may be screened for immunocompatibility with the patient before implantation. In other embodiments, the decellularised human scaffold may be repopulated with non-immunogenic cells, for example cell that have been engineered to remove surface antigens, such as HLA, that might elicit an immune response in an individual.

Other aspects of the invention provide a decellularised tissue scaffold produced by a method described above.

Decellularised tissue scaffolds produced as described herein are acellular and display the extracellular matrix pore structure, architecture and morphology of the source tissue sample. Decellularised tissue scaffolds produced from fibrotic source tissue samples display the increased ECM components and altered architecture and morphology characteristic of the source tissue.

The decellularised tissue scaffolds may be useful for disease modelling. Suitable scaffolds may be derived from normal tissue sample or pathological tissue sample, as described above.

A method of disease modelling may comprise;
  providing a decellularised tissue scaffold produced as described above, optionally repopulating the scaffold with cells to produce a re-cellularised tissue, and
  determining the effect of a compound, drug, biological agent, device or therapeutic intervention on the scaffold or tissue or the cells therein.

Methods described herein may be useful in modelling tissue diseases or diseases affecting the tissue, such as tissue fibrosis, tissue cancer and metastases, tissue drug toxicity, post-transplant immune responses, and autoimmune hepatitis.

The decellularised tissue scaffolds may also be useful for proteomics, biomarker discovery, and diagnostic applications. For example, the effect of a protease on the components, architecture or morphology of a decellularised tissue scaffold may be useful in the identification of biomarkers.

Another aspect of the invention provides a device for producing a decellularised tissue scaffold comprising
  (i) a cassette comprising;
    a chamber for accommodating a tissue sample immersed in decellularisation reagent,
    an inflow conduit for directing decellularisation reagent into the chamber, and
    an outflow conduit for directing decellularisation reagent out of the chamber,
  (ii) reagent reservoirs for decellularisation reagents, said reservoirs being connectable to the inflow conduit of the cassette,
  (iii) an oscillator for subjecting cassette to oscillation with a displacement of 1 mm or more and a frequency of 3 Hz or more, and
  (iv) a processor programmed to direct the pump and the oscillator to subject a sample in the chamber to a regime of one or more cycles of treatment with sets of different decellularisation reagents from the reservoirs under high frequency oscillation.

The device may further comprise;
  (v) one or more waste reservoirs for storage of decellularisation reagents following exposure to a tissue sample in the chamber, said reservoirs being connectable to the outflow conduit.

The device may further comprise;
  (vi) an inlet port to allow the entry of decellularisation reagents into the inflow conduit and
  (vii) an outlet port to allow exit of decellularisation reagents from the outflow conduit.

The device may further comprise;
  (viii) one or more sensors for measuring or monitoring conditions in the sample chamber.

The pressure, volume, flow pattern, temperature, gases, pH, mechanical force, turbidity, concentration of a biological molecule or other parameter of the decellularisation reagent immersing the tissue sample may be determined.

Suitable sensors include pressure, volume, flow pattern, temperature, gases, pH, mechanical force and turbidity sensors.

In some embodiments, the device may further comprise;
(ix) one or more actuators for altering conditions in the sample chamber.

The one or more actuators may be operably linked to the one or more sensors, optionally via the processor, to alter the temperature, pressure, pH, turbidity or other parameter of the decellularisation reagent in the sample chamber in response to a measurement of the parameter by the sensor which falls outside a predetermined range.

The cassette comprises the chamber in which the tissue sample is immersed in the decellularisation reagents. The cassette may comprise a single chamber or multiple chambers, for example 2, 3, 4, 5, 6 or more chambers. In some embodiments, the chamber may comprise 6, 12, 18, 24, 30, 36, 42 or 48 or more chambers. The multiple chambers may be disposed within the cassette in any arrangement, for example in 2 dimensional (i.e. horizontal or vertical) arrays or 3 dimensional arrays. Multiple chambers may be useful for processing multiple tissue samples in parallel.

The cassette may have any suitable size. For example, a cassette may have dimensions of 100-400 mm, 500-600 mm×50-80 mm (width×length×height), such as 305 mm×650 mm×65 mm.

In some embodiments, the chamber may contain a tissue sample. A tissue sample in the chamber may be immersed in decellularisation reagent introduced into the chamber from the reservoir through the inflow conduit.

The cassette may further comprise an inlet port for the introduction of decellularisation reagents to the inflow conduit and an outlet port for the removal of decellularisation reagents from the outflow conduit.

Preferably, the cassette comprises a single inlet port and a single outlet port. This may be useful in minimising the external contamination risk by reducing the number of connections required.

In some preferred embodiments, multiple chambers in the cassette may be linked to the inlet port via the inflow conduit and linked to the outlet port via the outflow conduit. For example, the inflow conduit may be branched to operably connect the inlet port to multiple chambers i.e. the conduit may be connected to the inlet port in unitary form and may then divide into different branches, each chamber being operably connected to a different branch of the inflow conduit, so that the flow of decellularisation reagents entering the cassette through the inlet port divides between the different branches of the conduit and enters the different chambers. Similarly, the outflow conduits may be branched to connect the multiple chambers to the outlet port, each chamber being operably connect to a different branch of the outflow conduit, which merge to form a unitary conduit at the outlet port. The flow of decellularisation reagents exiting the different chambers into the branches of the outflow conduit merges into a single flow which passes through the outlet port.

The branched inflow and outflow conduits allow uniform filling of the chambers in the cassette by dividing the flow of decellularisation reagents entering the cassette via the inlet port equally between the chambers.

In some preferred embodiments, the cassette may comprise three plates (the base, centre and head plates).

The plates may be separated by gaskets or o-rings which form a seal between the plates to prevent leakage and cross-contamination of reagents and maintain sterility.

The plates may be shaped to form the chambers and inflow and outflow conduits when they are brought together to form cassette.

The centre plate of the cassette may comprise one or more chambers for tissue samples. For example, the centre plate may comprise an array of chambers.

The size of the chambers is determined by the size of the samples to be accommodated. The number of chambers in the centre plate may be increased or reduced to allow for the accommodation of tissue samples of different sizes.

The base plate of the cassette may comprise an inlet port and inflow conduits to connect the port to the one or more chambers in the centre plate. The inflow port has an open position to allow the sample chambers to be filled with decellularisation reagent through the inflow conduits and a closed position to prevent leakage from the inflow conduits at other times.

The base plate of the cassette may further comprise an outlet port and outflow conduits to connect the one or more chambers in the centre plate to the port. The outflow port has an open position to allow the decellularisation reagent to be drained from the sample chambers through the outflow conduits and a closed position to prevent leakage of reagent from the outflow conduits at other times.

The inflow and outflow conduits may be formed from channels, tunnels or grooves in the body of the base plate.

The base plate may be shaped to prevent a tissue sample in chamber in the centre plate from entering the conduits in the base plate, whilst allowing the decellularisation reagents to access the chamber from the conduits. For example, the base plate may comprise an extrusion or baffle at the centre of each channel.

In some embodiments, the cassette may comprise a membrane within the centre of the channel which allows the movement of liquid between the conduits in the base plate and the chambers in the centre plate, but prevents a tissue sample in chamber in the centre plate from entering the conduits in the base plate. The membrane may be positioned in the base plate, the centre plate or between the plates.

In the assembled cassette, the one or more chambers in the centre plate are positioned over the conduits in the base plate, such that each chamber is operably linked to a branch of the inflow conduit and a branch of the outflow conduit.

The cassette may further comprise the one or more sensors and/or actuators. For example, the sensors and/or actuators may be located in the base, centre and/or head plate of the cassette.

The head plate may comprise a pattern of conduits that corresponds to the pattern of conduits in the base plate. These conduits allow gas exchange from the sample chambers during the filling and draining of decellularisation reagents. During filling, when the outflow conduit is closed, the head plate conduits provide a path for air to be displaced from within the cassette. Likewise, when draining and the inflow conduit is closed, air must displace the reagents that are being drained from the cassette. The conduits may be connected to appropriate filters to allow for sterile gaseous exchange and the prevention of over-pressurisation in the cassette.

In the centre of each conduit within the head plate, there is an extrusion which has been designed to prevent liquid from entering the channels in the head plate. The extrusion is disposed to encourage reagent to drip back into the sample chamber in the centre plate, and not pass into the head plate.

For example, the extrusion may have a substantial conical shape, with the apex facing the centre plate. In addition, a membrane may be positioned within the centre of the channel. The membrane may for example allow gaseous movement but not liquid movement between plates.

The head plate may be shaped to prevent decellularisation reagents from entering the conduits in the head plate, whilst allowing the decellularisation reagents to access the chamber from the conduits. For example, the head plate may comprise an extrusion or baffle at the centre of each channel.

The head plate may further comprise one or more sampling ports to allow access to the one or more chambers in the centre plate. This may be useful for reagent sampling from each chamber in order to assess reagent composition. The level of particular molecules of interest, for example in the reagent or the sample, may be monitored. The sterility of the chamber may also be monitored through the sampling port.

A reagent reservoir is a container for a decellularisation reagent. The device may comprise a separate reagent reservoir for each decellularisation reagent that is used in the treatment regime. Preferably, the device comprises at least four reagent reservoirs to allow the treatment of the tissue sample with at least four different decellularisation reagents.

The reagent reservoirs may be operably linked to the inlet port, such that reagents from the reservoirs can be introduced to one or more chambers through the inflow conduit. For example, the reagent reservoirs may be connected to the inlet port of the cassette by tubing and manifolds in accordance with standard techniques. Appropriate tubing, adapters and connectors to connect the reagent reservoirs to the inlet port of the cassette are readily available from commercial sources.

The reagent reservoirs may contain decellularisation reagents, such as osmotic agents, detergents, wash solutions and protease, as described above.

The device may further comprise a waste reagent reservoir. The waste reagent reservoir may be operably linked to the outlet port. The waste reagent reservoir may receive used decellularisation reagents from the outlet port.

During the removal of waste decellularisation reagents to the waste reservoir, preferably air replaces the removed reagent in the chamber and conduits via an inlet in the cassette. The waste reagent reservoirs may be connected to the outlet port of the cassette by tubing and manifolds in accordance with standard techniques. Appropriate tubing, adapters and connectors to connect the waste reagent reservoir to the outlet port of the cassette are readily available from commercial sources.

The cassette is operably linked to the oscillator. For example, the cassette may sit in a supportive chassis that is connected to the oscillator.

The oscillator is adapted to subject the cassette to high frequency oscillation (e.g. 3 Hz or more). Suitable oscillators are well-known in the art.

Preferably, other components of the device, such as reagent reservoirs, pumps, tubing, and processor are not oscillated.

In use, decellularisation reagent moves from a reagent reservoir and enters the cassette through the inlet port. From the inlet port, the decellularisation reagent moves through the inflow conduit to the chamber, where it immerses the tissue sample. After treatment of the tissue sample, the decellularisation reagent moves through the outflow conduit to the outlet port. The decellularisation reagent exits the cassette through the outlet port and enters the waste reservoir. Fresh decellularisation reagent may then be introduced into the chamber through the inflow conduit, in accordance with a decellularisation regime described herein.

The movement of decellularisation reagents through the device may be driven by any convenient means, including a pump, air pressure or gravity. In some preferred embodiments, the device comprises a pump to drive the movement of the decellularisation reagent. Preferably, each reagent reservoir of the device has a separate pump. This allows the movement of the decellularisation reagents in each reservoir to be individually controlled.

The device may be adapted to maintain a sterile environment in the chamber for the tissue sample. Sterility may be maintained during decellularisation using a variety of techniques known in the art, such as controlling and filtering the air flow and/or perfusion with antibiotics, anti-fungals or other anti-microbials to prevent the growth of unwanted microorganisms. Suitable anti-microbial compounds are well-known in the art.

The device may be adapted to monitor parameters of the movement of the decellularisation regime (e.g. pressure, volume, flow pattern, temperature, gases, pH, mechanical forces). For example, the system may comprise sensors that monitor the decellurisation reagents and/or the tissue sample. Sensors may be used to monitor the pressure of a decellurisation reagent moving through the device; the ambient temperature in the system and/or the temperature of the tissue sample or decellurisation reagents; the pH and/or the rate of flow of a decellurisation reagents moving through the device; and/or a biological parameter of a tissue sample in the chamber. In addition to having sensors for monitoring such features, the device may comprise include controls or actuators for maintaining or adjusting such features.

Controls may include components such as a thermometer, a thermostat, electrodes, pressure sensors, overflow valves, valves for opening and closing fluid connections to decellularisation reagents and altering rates and directions of flow.

To ensure constant conditions (e.g. temperature), the chambers, reservoirs and tubing may be water-jacketed, or placed upon a heating plate.

The device may comprise a processor for controlling the decellurisation of a tissue sample in the chamber. The processor may be a programmable control unit (e.g. a laptop or stand-alone computer, or integrated computer device) which defines the variables of the decellularisation regime, including oscillation rate, period of oscillation, pump rate, pump activity duration, as well as the monitoring and feedback based control of temperature, pressure, pH, and flow rate. The processor may receive and process information from one or more of the sensors in the device. The processor may transmit information and instructions back to the bioreactor and/or the tissue sample.

The processor may allow for the storage and implementation of a range of pre-programmed decellurisation methods, controlling all appropriate conditions, as well as manual operation of process variables. For example, the processor may be adapted or programmed to calculate exposure times and oscillation speeds for each decellularisation reagent according to a decellularisation method as described herein for that particular tissue sample, based on the weight of tissue sample. The processor may change the decellularisation reagent and alter the rate of flow or pressure of the decellularisation reagents, via one or more pumps and/or valve controls in the system.

In some embodiments, the processor may vary conditions in the sample chamber in response to a sensor, for example a sensor monitoring biological molecules. For example, reagents may be changed when a particular molecule concentration within the sample chamber surpasses a defined threshold.

Various further aspects and embodiments of the present invention will be apparent to those skilled in the art in view of the present disclosure.

Other aspects and embodiments of the invention provide the aspects and embodiments described above with the term "comprising" replaced by the term "consisting of" and the aspects and embodiments described above with the term "comprising" replaced by the term "consisting essentially of".

It is to be understood that the application discloses all combinations of any of the above aspects and embodiments described above with each other, unless the context demands otherwise. Similarly, the application discloses all combinations of the preferred and/or optional features either singly or together with any of the other aspects, unless the context demands otherwise.

Modifications of the above embodiments, further embodiments and modifications thereof will be apparent to the skilled person on reading this disclosure, and as such these are within the scope of the present invention.

All documents and sequence database entries mentioned in this specification are incorporated herein by reference in their entirety for all purposes.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Certain aspects and embodiments of the invention will now be illustrated by way of example and with reference to the figures described below.

FIG. 1 shows 5 mm$^3$ liver tissue cubes before (top left) and after (bottom left) decellularisation. H&E (Haematoxylin and Eosin) histological staining showed removal of cells after decellularisation. SR (Sirius Red) staining showed preservation of collagen (red) and removal of cellular materials (yellow) in decellularised tissue.

Figure 6:
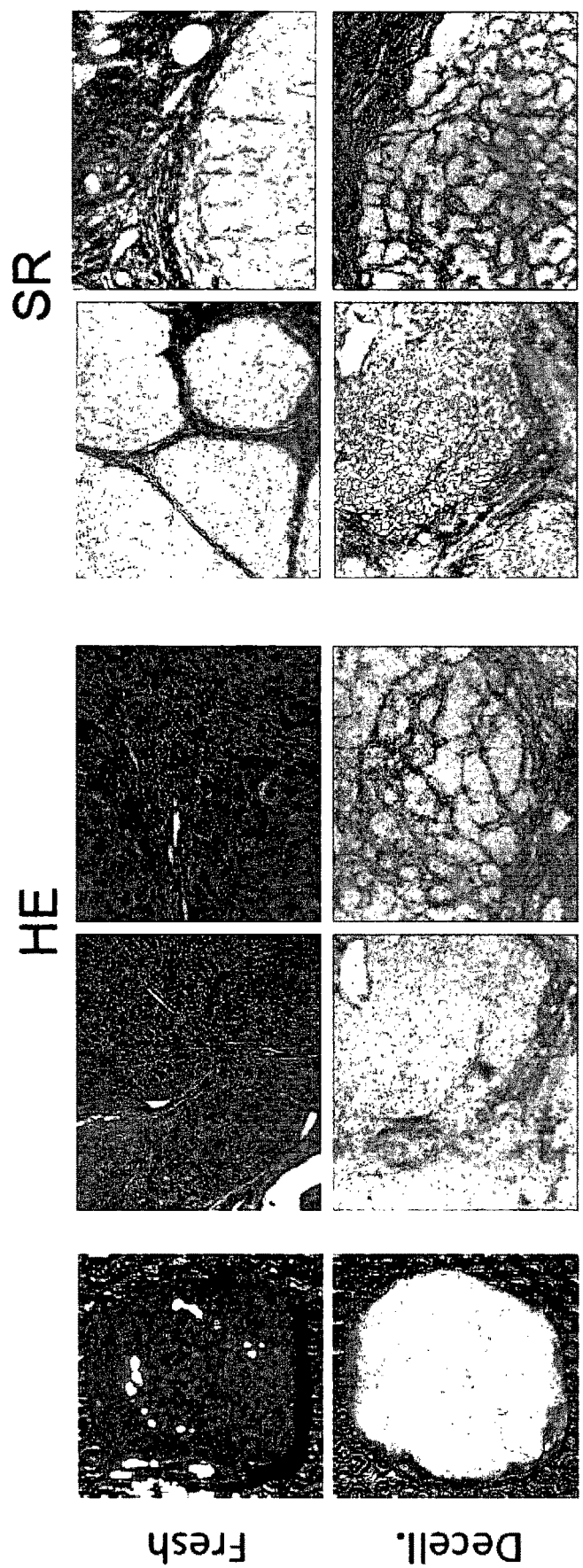

FIG. 6 shows 5 mm$^3$ cirrhotic liver tissue cubes before (top left) and after (bottom left) decellularisation. H&E (Haematoxylin and Eosin) histological staining showed removal of cells after decellularisation. SR (Sirius Red) staining showed preservation of collagen (red) and removal of cellular materials (yellow) in decellularised tissue.

Figure 7:
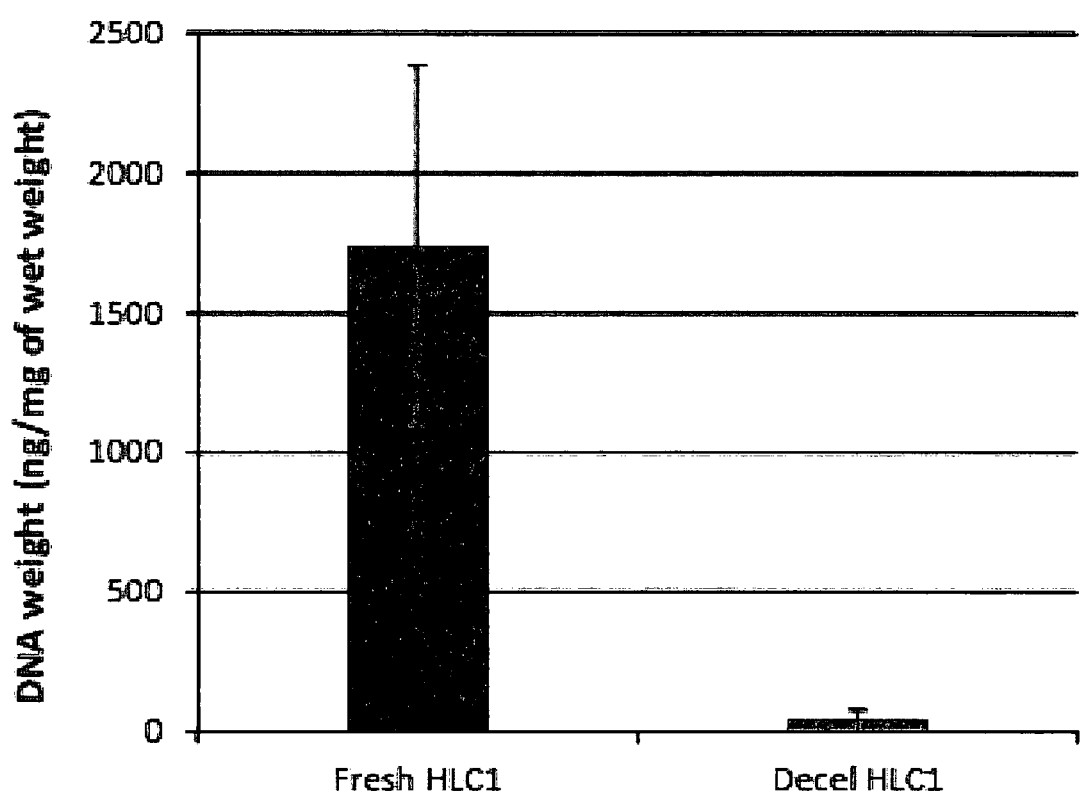

FIG. 7 shows quantification of DNA (cirrhotic liver). The decellularisation procedure was efficient with a marked decrease in DNA content ($p<0.01$).

Figure 8:
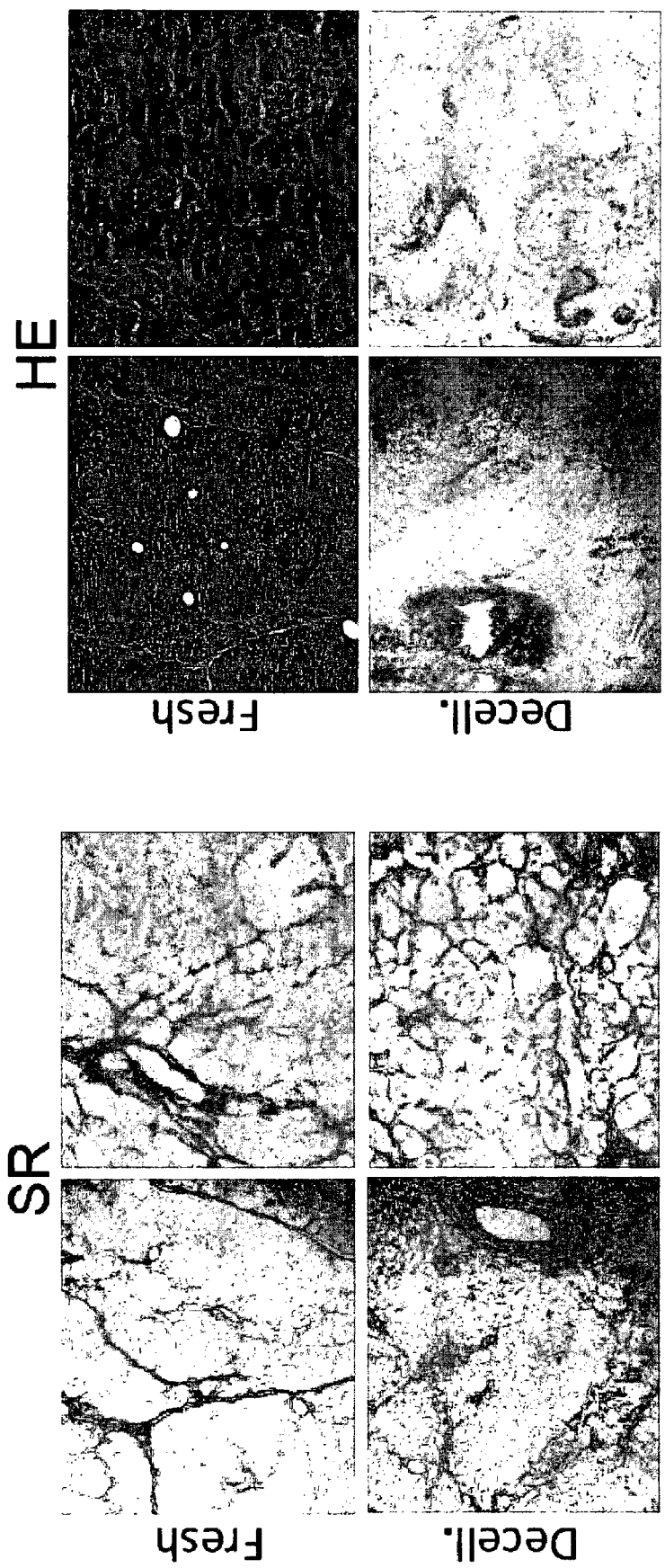

FIG. 8 shows histological comparison of pancreatic tissue before and after decellularisation. SR (Sirius Red) staining showed preservation of collagen (red) and removal of cellular materials (yellow) in decellularised tissue. H&E (Haematoxylin and Eosin) histological staining showed removal of cells after decellularisation.

Figure 9:
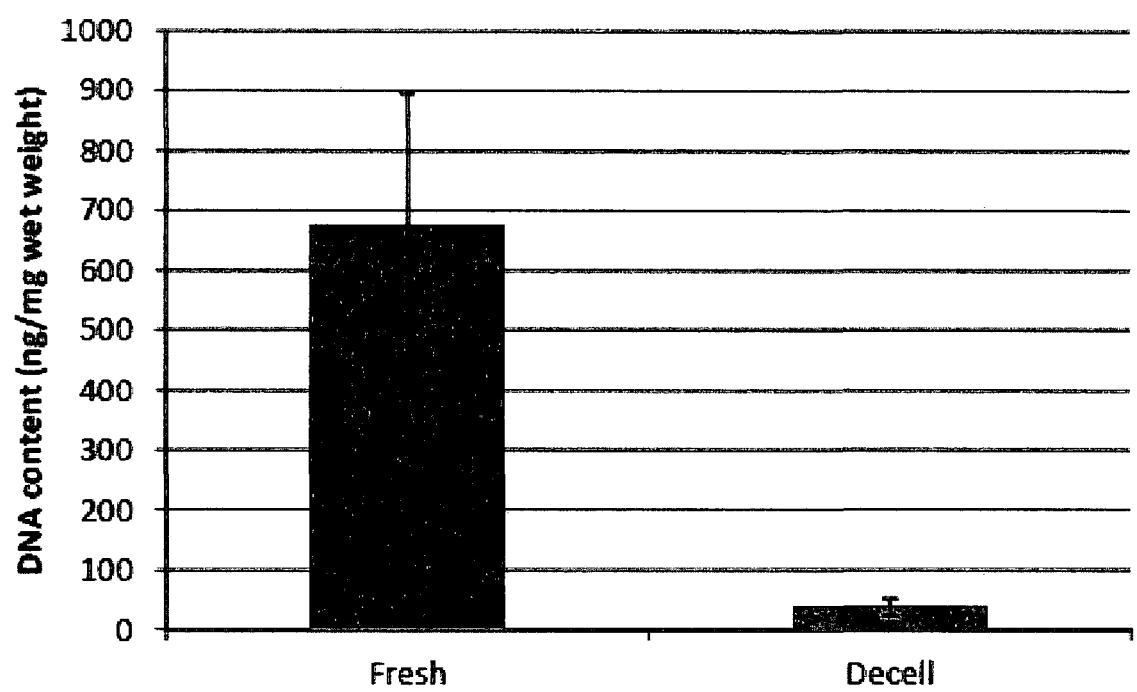

FIG. 9 shows quantification of DNA (pancreas). The decellularisation procedure was efficient with a marked decrease in DNA content ($p<0.01$).

Figure 10:
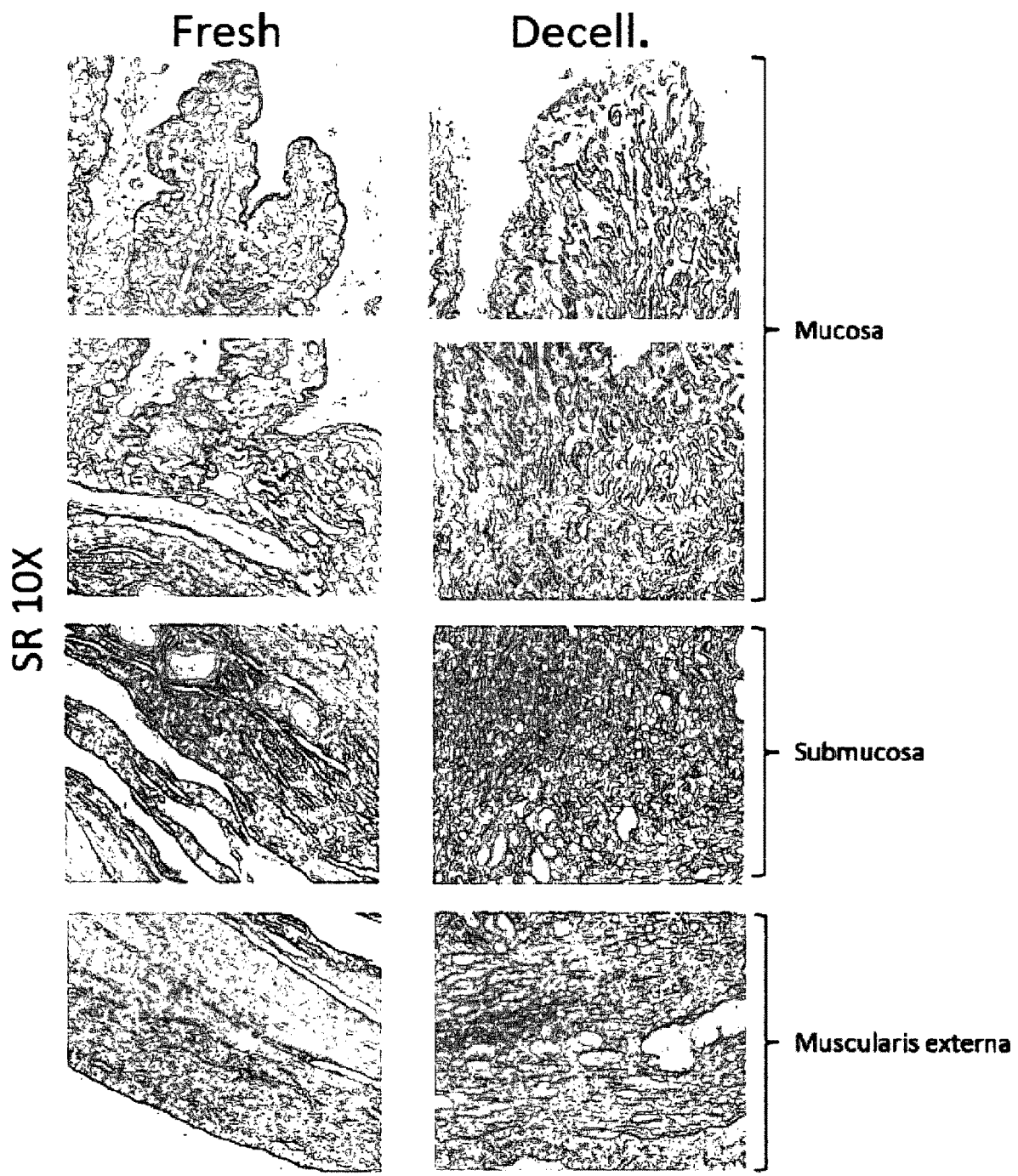

FIG. 10 shows histological comparison of human intestine before (left) and after decellularisation (right) showing preservation of collagen structures in all the layers of the tissue after the decellularisation procedure.

Figure 11:
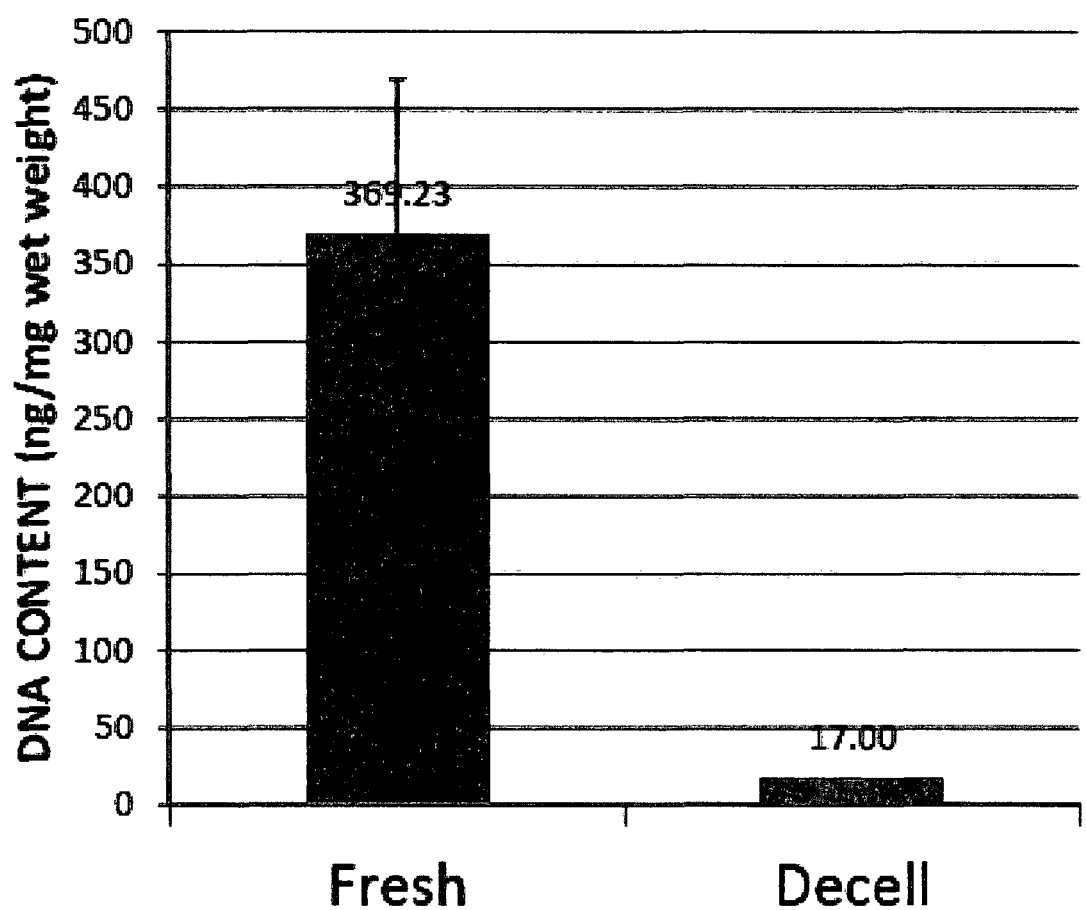

FIG. 11 shows quantification of DNA (intestine). The decellularisation procedure was efficient with a marked decrease in DNA content ($p<0.01$).

Figure 12:
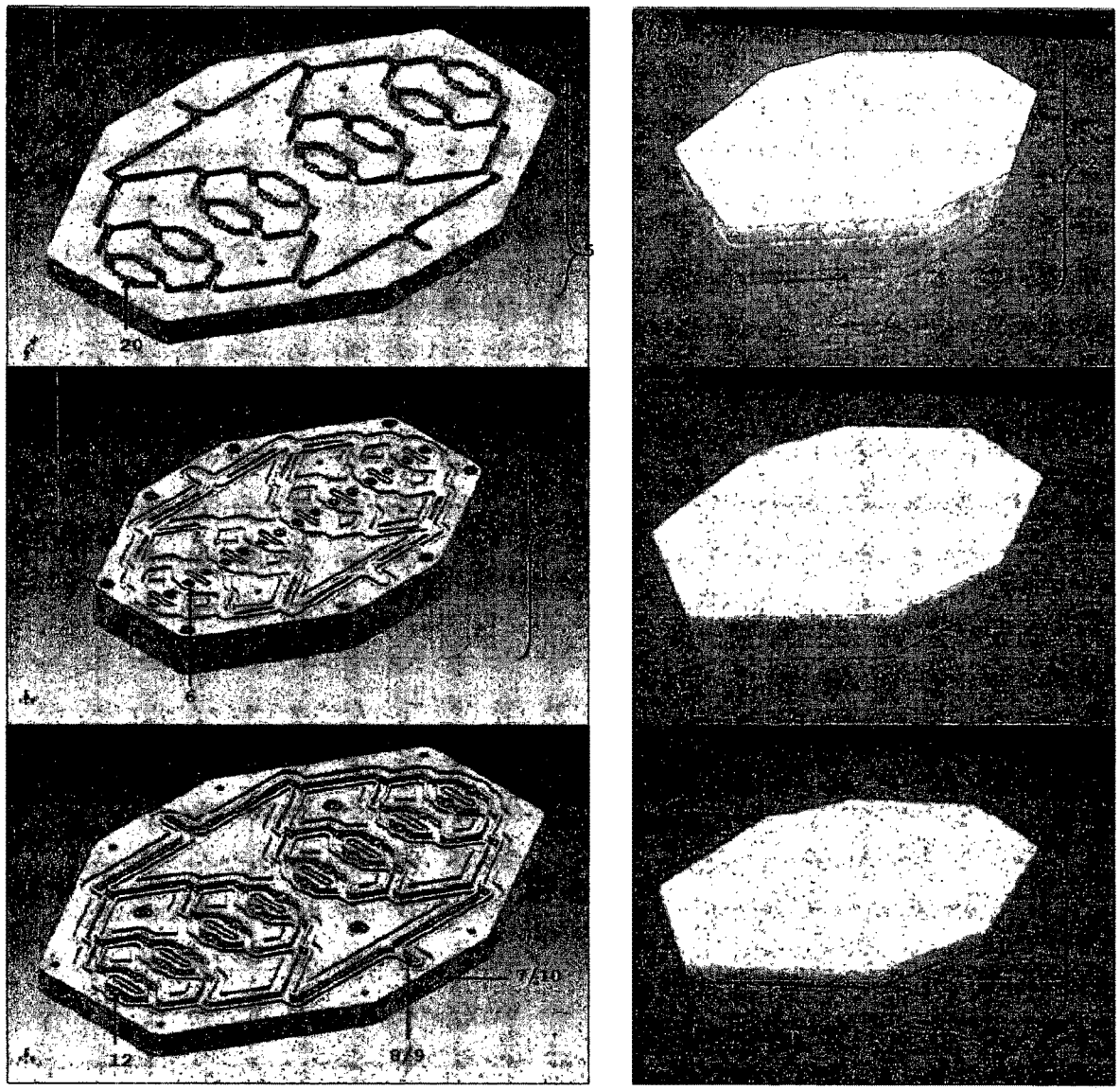

FIG. 12 shows 3D CAD models of the head (A), centre (B) and base (C) plates produced using Autodesk Inventor Professional 2014 software. Panel (D) depicts the 3D printed, fully assembled cassette. Panels (E) and (F) depict the conjoined base and centre plate and the base plate alone, respectively.

DETAILED DESCRIPTION

An embodiment of a device for decellularising tissue samples as described herein is shown in FIG. 12. The device consists of a series of reagent reservoirs (not shown) that house the decellularisation reagents required during process operation. The reservoirs connect to a cassette 2 via tubing (not shown). The tubing is associated with a reagent driving pump (not shown). The reagents enter the cassette 2 via an inlet port 7 that is situated in a base plate 3 of the cassette 2, before travelling along an inflow conduit 8 and being equally divided between multiple sample chambers 6 located in a centre plate 4 of the cassette 2. To enter the sample chambers 6, decellularisation reagents must either flow through appropriate membranes (not shown) and/or past extrusions 12 that retain the sample within the chambers 6 located in the centre plate 4. The entire cassette 2 is then oscillated by the oscillating motor (not shown), in accordance with the decellularisation protocol. Reagents are then drained from the cassette 2 via the outflow conduit 9 in the base plate, before exiting the cassette through the outlet port 10 and progressing toward the external waste reservoir (not shown) via tubing and associated driving pump(s) (not shown). During draining, the removed reagents are replaced with filtered air that enters the cassette via a series of conduits in the head plate 5 of the cassette 2. Reagents are prevented from entering these conduits via hydrophobic membranes (not shown) and/or extrusions 20 in the head plate 5. During stationary phases of the process, the reagents and/or tissues may be sampled via integrated sampling ports (not shown) for off-line process assays. The whole process is controlled via a processor (not shown) that allows for control of all aspects of the process, both predetermined and in response to feedback loops.

Experiments

1. Determining G Force

The novel system used for decellularising biological tissue is considered to be a simple harmonic oscillator as there is only one force acting on the system in a periodic motion where the restoring force is directly proportional to the displacement and acts in the direction opposite to that of the displacement, with a constant amplitude and frequency. From this statement we can build an equation, which will allow us to calculate the G-force experienced by the tissue and reagents during decellularisation. Therefore, a biological tissue undergoing harmonic motion with frequency f Hz and amplitude Û m and assuming it starts at zero displacement (i.e. x=0 and t=0) will occupy the position x=Û sin(f*2*n*t) (considering the difference in density between the tissue and it surrounding solution is negligible). Furthermore, a particle (or tissue in this case) which moves under simple harmonic motion will have the equation x"=−w2x, where w=2*pi*f. Substituting these equation into Newton second law, Force (F) equals mass (m) multiplied by acceleration (a) [F=ma], results in the equation F=−m[(2*n*f)2] *Û sin(f*2*n*t). This is extremised when |sin|=1. Therefore, it will be at its maximum/minimum when F=+/−Ûm[(2*n*f)2]. Finally by dividing the equation by the force experienced by gravity (mg), the equation for G-force=(Û/g)*[(2*n*f)2].

2. Reagents

Abbreviations; SdC Sodium Deoxycholate; PBS/AA PBS+Antibiotic Antimycotic; T/E 0.025% Trypsin/EDTA 0.025%; SDS Sodium Dodecyl Sulfate; TX100 Triton X 100; RT Room Temperature; PAA Paracetic Acid; EtOH Ethanol.

Sodium deoxycholate solution (SDS) 4%: 40 g of Sodium deoxycholate, BioXtra, ≥98.0% (Sigma-Aldrich) is added to 1 L of deionized water (MilliQ by Millipore), and stirred using a magnetic stirrer for 1 hr.

Saline Solution 8.7%: 87 g of Sodium Chloride, >99% (Sigma-Aldrich) is added to 1 L of deionized water (MilliQ by Millipore), and stirred using a magnetic stirrer for 1 hr.

Reagent Mixture Solution (SDC3%; SDS 0.5%; TX1000.3%; T/E0.025%; NaCl 4.3%): 30 g of Sodium deoxycholate, BioXtra, ≥98.0% (Sigma-Aldrich), 5 g of Sodium dodecyl sulfate, BioXtra, ≥99.0 (Sigma-Aldrich), 3 ml of Triton X-100 (Sigma-Aldrich), 10 ml of 0.25% Gibco® Trypsin-EDTA (Life technologies) and 43 g of Sodium Chloride (Sigma-Aldrich) are added to deionized water (MilliQ by Millipore) to make a total of 1 L and stirred using a magnetic stirrer.

Peracetic acid (PAA) 0.1%: 1 ml of Peractic acid solution, purum, ~39% in acetic acid (Sigma-Aldrich) is added to 1 L of deionized water (MilliQ by Millipore), and stirred using a magnetic stirrer for 1 hr.

Ammonium Hydroxide ($NH_4OH$) 0.1%: 1 ml of Ammonium hydroxide solution, ACS reagent, 28.0-30.0% NH3 basis (Sigma-Aldrich) is added to 1 L of deionized water (MilliQ by Millipore), and stirred using a magnetic stirrer for 1 hr.

3. Methods 3.1 Tissue Decellularisation

The protocols for decellularising biological tissue are described elsewhere herein and shown in Tables 2 and 3.

After the completion of a protocol, random samples are selected and; fixed in 10% formalin for histological and immunohistochemistry studies, snap-frozen in liquid nitrogen and stored at −80° C. freezer until needed for the DNA, collagen and elastin quantification assays, fixed in 2.5 Glutaraldehyde for SEM imaging or stored in 1% PBS at 4° C. until needed for bioengineering experiments.

Initially liver cubes are thawed in a water bath at 37° C. for 1 hour (hr), followed by the addition of 1.2 ml of 1% PBS for 15 minutes (mins). Once thawed the cubes are transferred into 2 ml safe-lock tubes (Eppendorf). A standardised 1.5 ml of each solution is added to its respected tube/protocol.

3.2 Histology and Immunohistochemistry

Tissue samples, previously fixed in 10% formalin, were retrieved, washed in distilled water, dehydrated in a series of Industrial Denatured Alcohol (IDA) (Acquascience) and xylene baths and finally embedded in paraffin. The samples were then sliced into 5 μm sections using a Leica RM2035 microtome (Leica Biosystems). All sections were then passed through three histology grade xylene (Acquascience) baths for a minimum of 5 mins, and then through three IDA (Acquascience) baths for a minimum of 2 mins, finally ending up in tap water.

3.3 Histology

Sections were stained at room temperature as follows:

Haematoxylin and Eosin: Sections were treated with haematoxylin Harris' formula (Leica biosystems) for 10 mins and then washed in tap water for 5 mins. Next, the sections were stained with eosin (Leica biosystems) for 3 mins, and then washed again with water. The sections were then dehydrated through IDA (Industrial Denatured Alcohol) (Acquascience) as quickly as possible and then placed in histology grade xylene (Acquascience) until mounted.

Pico-Sirius Red: Sections were treated with freshly filtered pico-sirius red—F38 (R. A. Lamb; CI-35780) for 20 mins. The section were then dehydrated through IDA (Acquascience) as quickly as possible and then placed in histology grade xylene (Acquascience) until mounted.

Elastic Van Gieson: Sections were treated with 0.5% potassium permanganate for 5 mins and washed thoroughly with distilled water. Next, they were treated with 1% oxalic acid for 1 minute, washed with distilled water followed by absolute alcohol. Sections were then stained with neat Miller's Elastic—(R. A. Lamb; LAMB/080D) for 2 hrs, washed thoroughly with 70% industrially methylated spirits (IMS) (Fisher scientific) and then placed in tap water. The sections were checked under the microscope and, if necessary, differentiated in 0.5% acid-alcohol (1% HCl in 70% IDA aq.). As a final step, the sections were stained with van Gieson (Leica biosystems) for 5 mins. The section were then dehydrated through IDA (Acquascience) as quickly as possible and then placed in histology grade xylene (Acquascience) until mounted.

3.4 Immunohistochemistry

Slides were incubated in 0.5% Trypsin (MP Biomedical)/0.5% Chymotrypsin (Sigma)/1% Calcium Chloride (BDH) in 10% Tris buffered saline (TBS) for 30 minutes at 37° C. Slides were then washed in 10% TBS at pH 7.6 with 0.04% Tween-20 (Sigma) for 5 mins. The slides were later blocked in peroxide blocking solution (Novocastra) for 5 minutes and incubated for 1 hour in the following primary antibodies; collagen I (Rabbit pAb to coll1 (ab34710), diluted 1:200; abcam), collagen III (Rabbit pAB to coll3 (ab7778), diluted 1:500; abcam), collagen IV (mouse mAb to coll4 (M0785), diluted 1:25; Dako), fibronectin (mouse mAb to fibronectin (MAB1937), diluted 1:100; Millipore) and laminin (mouse mAb to laminin α5-chain (MAB1924), diluted 1:200; Millipore). The slides were then placed for 25 minutes in Novolink™ post primary (Novocastra), 25 mins in Novolink™ polymer solution (Novocastra) and developed with Novolink™ 3,3' di-amino-benzidine (Novocastra). The slides were finally counterstained with Mayer's Haematoxylin (Sigma) for 1 mins.

All sections were mounted with DPX (leica biosystems); cover slipped and observed using a Zeiss Axioskop 40. Images were captured with an Axiocam IcC5 using Zeiss Axiovision (verison 4.8.2). All images were analysed and enhanced using Fiji v1.49d (ImageJ Jenkins server).

3.5 DNA Quantification

Decellularised tissue cubes used for all protocols were retrieved from the −80° C. freezer and thawed in a 37° C. water bath for 1 hr. The liver cubes were then weighed and if necessary, cut to be between 15 and 25 mg in weight. The cubes were then placed in 1.5 ml microcentrifuge tubes. Twenty μl of proteinase K was added to each, and then mixed thoroughly using a vortex. The cubes were then placed into a heating block at 56° C. for at least 16 hrs or until cubes were completely lysed. The DNA was then extracted using the QIAGEN DNAeasy Blood and Tissue Kit according to the manufacturer's instructions. The extracted DNA was eluted in 200 µl of buffer AE and was quantified using a NanoDrop ND-2000 spectrophotometer.

3.6 Collagen Quantification

The collagen content of native tissue and decellularized tissue was quantified using the total collagen assay kit according to the manufacturer's manual (QuickZyme Biosciences, The Netherlands). Briefly, samples were hydrolysed in 6M HCl at 95° C. for 20 hours, the hydrolysates were mixed with a chromogen solution staining the hydroxyproline residues and color was developed at 60° C. for 1 hour. The absorbance for each sample was determined at 555 nm using a FLUOstar Omega microplate reader (BMG labtech, Germany) and the collagen quantity was calculated by usage of a standard curve of pure collagen hydrolysates.

3.7 Scanning Electron Microscopy (SEM)

Samples were fixed in 2.5% glutaraldehyde in 0.1 M phosphate buffer and left for 24 hours at 4° C. Following washing with 0.1 M phosphate buffer, samples were cut into segments of approximately 1 cm length and cryoprotected in 25% sucrose, 10% glycerol in 0.05 M PBS (pH 7.4) for 2 hours, then fast frozen in Nitrogen slush and fractured at approximately −160° C. Next, samples were then placed back into the cryoprotectant at room temperature and allowed to thaw. After washing in 0.1 M phosphate buffer (pH 7.4), the material was fixed in 1% OsO4/0.1 M phosphate buffer (pH 7.3) at 3° C. for 1½ hours and washed again in 0.1 M phosphate buffer (pH 7.4). After rinsing with dH2O, specimens were dehydrated in a graded ethanol-water series to 100% ethanol, critical point dried using $CO_2$ and finally mounted on aluminum stubs using sticky carbon taps. The fractured material was mounted to present fractured surfaces across the parenchyma to the beam and coated with a thin layer of Au/Pd (approximately 2 nm thick) using a Gatan ion beam coater. Images were recorded with a 7401 FEG scanning electron microscope (Jeol, USA)

3.8 Bioengineering Procedure

Biological scaffolds were kept overnight in complete medium [day-1]. Cells were re-suspended at a concentration of 2 million cells per 50 µl (2×106/50 µL) per scaffold (n≥12 per cell line). Cells were drawn up in a 0.5 ml insulin syringe and released drop by drop to finally cover the decellularised tissue. Seeded scaffolds were kept for 2 h in a humidified environment at 37° C. with 5% CO2 allowing cell attachment followed by addition of complete culture medium [day 0]. The culture medium was changed at day 1 and afterwards every 3 days. At days 7, 14 and 21 following seeding, the scaffolds were placed in 10% formaldehyde and assessed by histology and immunohistochemistry or fixed in 2.5% glutaraldehyde for SEM analysis.

4. Results

Figure 1:
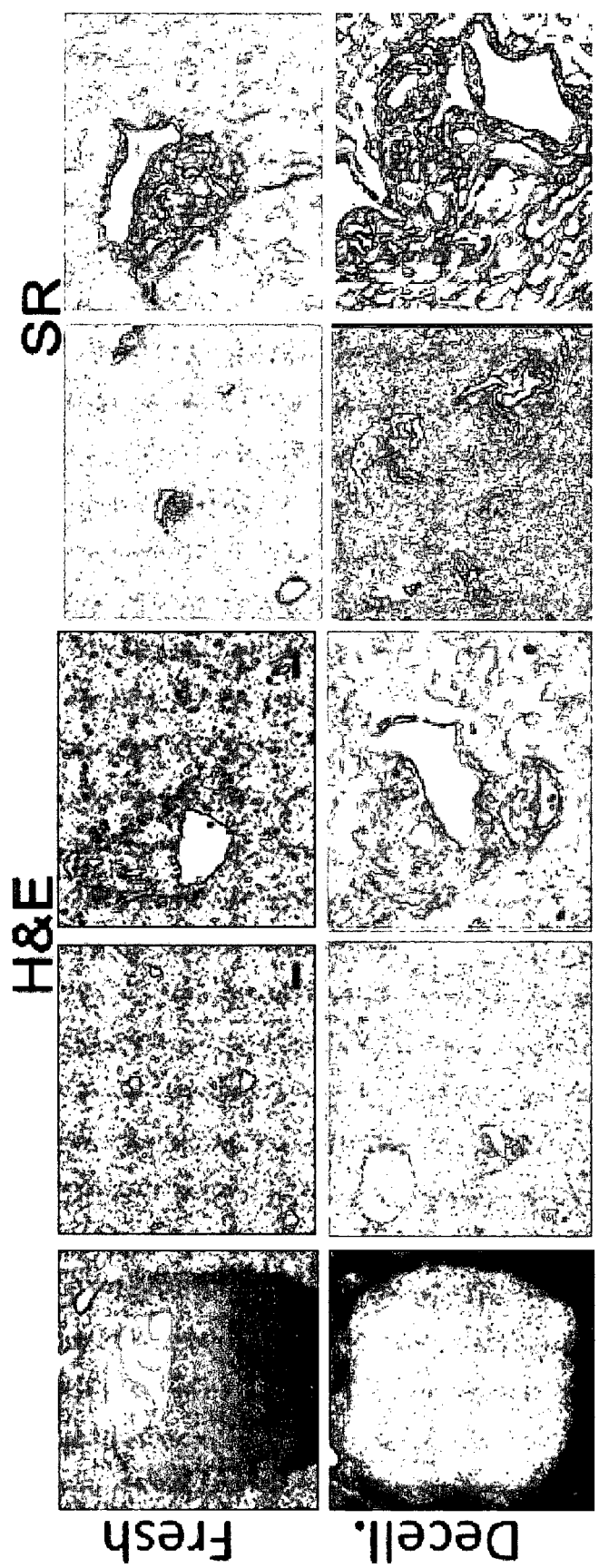
Figure 3:
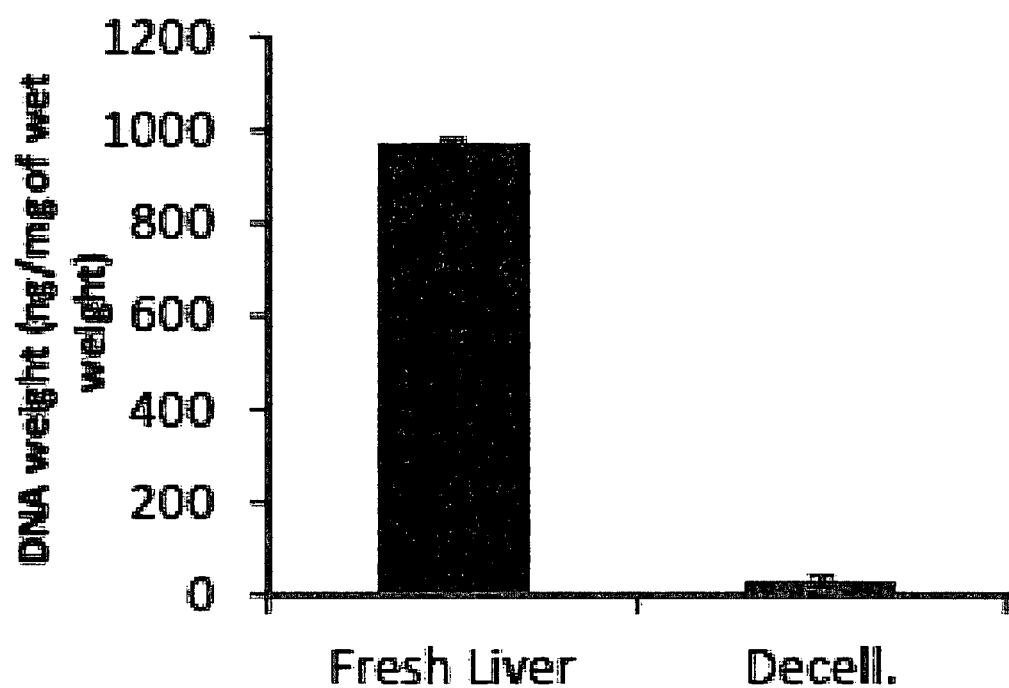
FIG. 3 shows quantification of DNA. The decellularisation procedure was efficient with a marked decrease in DNA content ($p<0.01$).

Decellularised healthy liver cubes (HL3, HL4, HL36 and HL43) were all macroscopically translucent and white in colour (FIG. 1). The vascular network was also visible and the tissue maintained its cubic structure. In addition, both native and decellularised liver tissue were inspected histologically for nuclear material (H&E staining) and cellular remnants (SR staining). The decellularisation protocols were successful at eliminating all cellular material (FIG. 1). This was confirmed by quantification the amount of DNA remaining in the decellularised liver cubes, which was significantly lower ($p<0.001$) that that of fresh liver tissue (FIG. 3).

Figure 2:
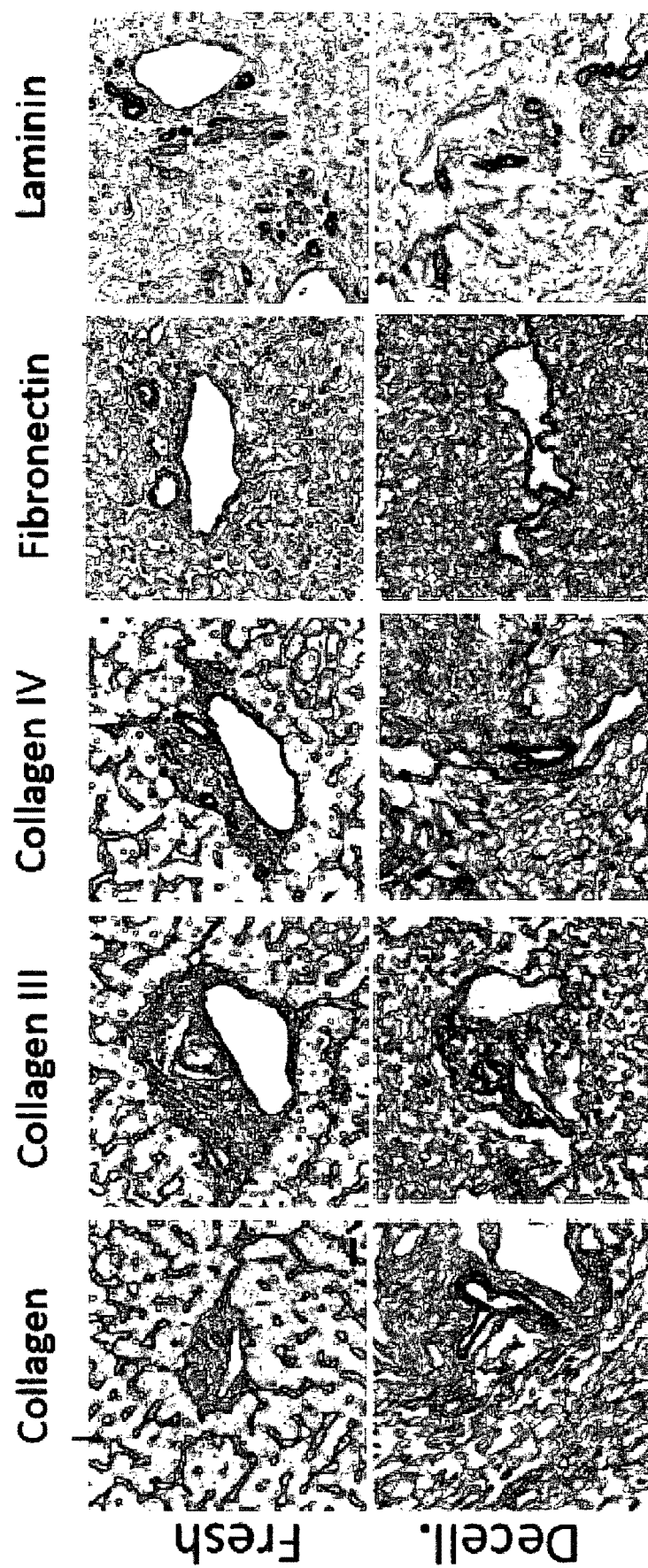
FIG. 2 shows immunohistochemistry analysis of extracellular-matrix proteins (ECM). Collagen I, III, IV (structural proteins) were preserved after decellularisation as well as laminin and fibronectin (basement membrane proteins)
Figure 4:
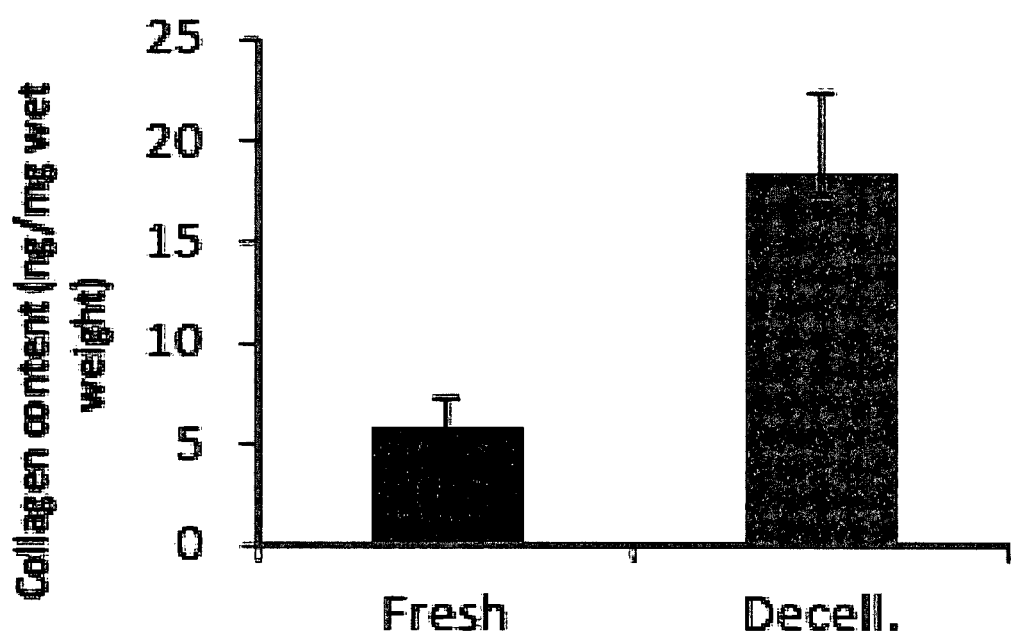
FIG. 4 shows quantitative measurement of collagen after decellularisation. Collagen quantification showed preservation of the amount of collagen in the decellularised tissue when compared to fresh tissue.

To investigate the retention of ECM proteins, immunohistochemistry was performed. Five ECM proteins were investigated, collagen I, collagen III, collagen IV, fibronectin and laminin (FIG. 2). Collagen I and III can be seen lining the portal tract area, while collagen IV and fibronectin was evident within the liver lobules. Laminin staining was positive around the vessels and bile duct. Similarly, collagen quantification demonstrated that the decellularised liver cubes were able to preserve collagen when compared to fresh tissue (FIG. 4).

Figure 5:
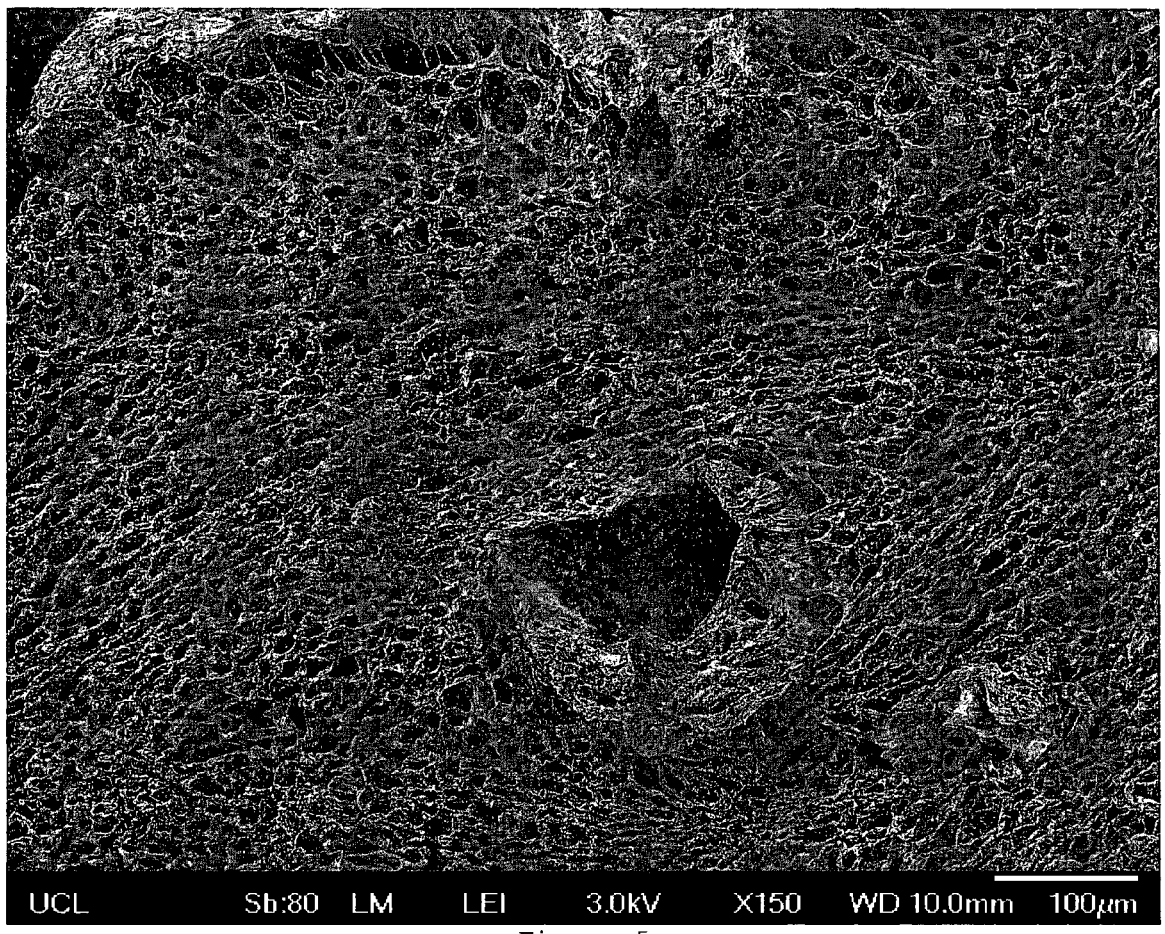
FIG. 5 shows 150× SEM image including a portal tract surrounded by a typical lobular structure. In addition, SEM image confirmed scaffold acellularity and clearly defined spaces once occupied by hepatocytes (i.e. hepatocyte-free spaces).

Furthermore, the decellularised liver cubes were analysed by scanning electron microscopy (SEM). The SEM images confirmed scaffold acellularity and showed the presence of clearly defined spaces once occupied by hepatocytes (i.e. hepatocyte-free spaces). The three-dimensional meshwork of connective tissue fibers structuring the hepatocyte-free spaces, as well as portal tracts and lobular structure, were found to be an exceptionally preserved (FIG. 5). To further investigate the mechanical properties of the scaffolds, the stiffness of the native tissue and decellularised tissue were measured using atomic force microscopy (AFM). This revealed no significant difference in stiffness between native and decellularised tissue.

Decellularised liver scaffolds were repopulated with different types of human liver parenchymal and non-parenchymal cells. These cells were found to exhibit excellent viability, motility and remodelling of the extracellular matrix. Furthermore, bioengineered scaffolds showed remarkable difference in gene expression when compared with standard 2D-system.

Decellularised cirrhotic liver tissue (HLC1) was similarly white in colour. Likewise, the vascular network was also visible and the tissue maintained its cubic structure. In addition, both native and decellularised cirrhotic liver tissue was inspected histologically for nuclear material (H&E staining) and cellular remnants (SR staining). The decellularisation protocols were successful at eliminating all cellular material (FIG. 6). This was confirmed by quantification the amount of DNA remaining in the decellularised liver cubes, which was significantly lower ($p<0.001$) that that of fresh cirrhotic liver tissue (FIG. 7).

The decellularised cirrhotic liver tissue was also able to retain the distorted hepatic architecture that characterizes fibrotic tissue. This can be seen in both the SR and H&E staining, which show well preserved nodules and fibrotic septa.

Decellularised pancreatic tissue was inspected histologically for nuclear material (H&E staining) and cellular remnants (SR staining). The decellularisation protocols were successful at eliminating most cellular material (FIG. 8). This was confirmed by quantification the amount of DNA remaining in the decellularised pancreatic cubes, which was significantly lower ($p<0.001$) that that of fresh pancreatic tissue (FIG. 9). The pancreatic architecture was also preserved. Both SR and H&E staining clearly show the preservation of the ECM where the Islets of Langerhans were situated (FIG. 8).

Finally, decellularised intestinal tissue was inspected histologically for cellular remnants (SR staining). The decellularisation protocols were successful at eliminating all cellular material (FIG. 10). This was confirmed by quantification the amount of DNA remaining in the decellularised intestinal cubes, which was significantly lower ($p<0.001$) that that of fresh intestinal tissue (FIG. 11). The intestinal microarchitecture was also preserved. SR staining visibly show the preservation of all four intestinal layers; villous mucosa, submucosa, muscularis externa and adventitia (FIG. 10).

TABLE 1

| System | TissueLyser LT | TissueLyser II |
|---|---|---|
| Mode of Agitation | Vertical | Horizontal |
| Oscillation (Hz) | 50 (0-50) | 30 (0-30) |
| Displacement (mm) | 9 | 24 |
| G-force (ms$^{-2}$) | 46.3↑ and −44.3↓ | 43.5 |
| G-force Equation | $=(\hat{U}/g) * [(2*pi*f)^2]$ | $=(\hat{U}/g) * [(2*pi*f)^2]$ |

TABLE 2

| Tissue ID | Protocol | Time (mins) |
|---|---|---|
| HL3 (125 mm$^3$) | 1. Deionised Water (MilliQ), 2 mins (repeat a total of 5 times)<br>2. RM, 2 mins<br>3. RM 4 mins (repeat a total of 2 times)<br>4. PBS 1%, 1 min<br>5. Saline Solution 8.7%, 2 mins (repeat a total of 5 times)<br>6. Repeat steps 1-3<br>7. PBS 1%, 5 mins (repeat a total of 3 times) | 66 |
| HL43 (125 mm$^3$) | 1. Deionised Water (MilliQ), 2 mins (repeat a total of 11 times)<br>2. RM, 2 mins<br>3. RM 4 mins (repeat a total of 2 times)<br>4. PBS 1%, 1 min<br>5. Saline Solution 8.7%, 2 mins (repeat a total of 5 times)<br>6. Repeat steps 1-3<br>7. PBS 1%, 5 mins (repeat a total of 3 times) | 76 |
| HL36 (125 mm$^3$) | 1. Deionised Water (MilliQ), 2 mins (repeat a total of 12 times)<br>2. RM, 2 mins<br>3. RM 4 mins (repeat a total of 2 times)<br>4. PBS 1%, 1 min<br>5. Saline Solution 8.7%, 2 mins<br>6. PBS 1%, 5 mins (repeat a total of 3 times) | 42 |
| HI5 (60-75 mm$^3$) | 1. Deionised Water (MilliQ), 2 mins (repeat a total of 5 times)<br>2. RM, 2 mins<br>3. RM 4 mins (repeat a total of 2 times)<br>4. PBS 1%, 1 min<br>5. Saline Solution 8.7%, 2 mins (repeat a total of 5 times)<br>6. Repeat steps 1-3<br>7. PBS 1%, 5 mins (repeat a total of 3 times) | 66 |
| Kidney (biopsy; 15.5 mm$^3$) | 1. Deionised Water (MilliQ), 2 mins (repeat a total of 5-10 times)<br>2. SDC 4% 2 mins (repeat a total of 5-10 times)<br>3. PBS 2 mins<br>These steps may be repeated one or more times | |
| Heart (biopsy; 8 mm$^3$) | 1. Deionised Water (MilliQ), 2 mins (repeat a total of 5-10 times)<br>2. SDC 4% 2 mins (repeat a total of 5-10 times)<br>3. PBS 2 mins<br>These steps may be repeated one or more times | |

TABLE 3

| Tissue ID | Protocol | Time (mins) |
|---|---|---|
| HL4 (216 mm$^3$) | 1. Deionised Water (MilliQ), 2 mins (repeat a total of 20 times)<br>2. RM, 2 mins<br>3. RM 4 mins (repeat a total of 2 times)<br>4. PBS 1%, 1 min<br>5. Saline Solution 8.7%, 2 mins (repeat a total of 5 times)<br>6. Repeat steps 1-3 (repeat a total of 2 times)<br>7. PBS 1%, 5 mins (repeat a total of 3 times) | 116 |
| HL43 (125 mm$^3$) | 1. Deionised Water (MilliQ), 2 mins (repeat a total of 10 times)<br>2. RM, 2 mins<br>3. RM 4 mins (repeat a total of 2 times)<br>4. PBS 1%, 1 min<br>5. Repeat steps 2-3<br>6. PBS 1%, 5 mins (repeat a total of 3 times) | 56 |
| HL36 (125 mm$^3$) | 1. Deionised Water (MilliQ), 2 mins (repeat a total of 10 times)<br>2. RM, 2 mins<br>3. RM 4 mins (repeat a total of 2 times)<br>4. PBS 1%, 1 min (repeat a total of 3 times) | 45 |
| HL-C1 (125 mm$^3$) | 1. Deionised Water (MilliQ), 2 mins (repeat a total of 20 times)<br>2. RM, 2 mins<br>3. RM 4 mins (repeat a total of 2 times)<br>4. PBS 1%, 1 min<br>5. Saline Solution 8.7%, 2 mins r(epeat a total of 5 times)<br>6. Repeat steps 1-3 (repeat a total of 2 times)<br>7. PBS 1%, 5 mins (repeat a total of 3 times)<br>8. Repeat step 2-3 | 166 |
| HP1 (125 mm$^3$) | 1. Deionised Water (MilliQ), 2 mins (repeat a total of 5 times)<br>2. RM, 2 mins<br>3. RM 4 mins (repeat a total of 2 times)<br>4. PBS 1%, 1 min(repeat a total of 2 times)<br>5. PAA 0.1%, 2 min (repeat a total of 2 times)<br>6. NH4OH 0.1%, 2 min (repeat a total of 3 times)<br>7. Deionised Water (MilliQ), 2 mins (repeat a total of 10 times)<br>8. Repeat steps 2-3<br>9. PBS 1%, 5 mins (repeat a total of 3 times) | 79 |

The invention claimed is:

1. A method of producing a decellularised tissue scaffold comprising;
   (i) providing a tissue sample selected from the group consisting of kidney, muscle, bone, adipose, cartilage, lung, bladder, cornea, skin, liver, spleen, placenta, intestine, pancreas, prostate, breast and heart,
   (ii) treating the tissue sample with an osmotic reagent, and
   (iii) treating the tissue sample obtained from step (ii) with a detergent,
   wherein steps (ii) and (iii) are repeated, and wherein the tissue sample is subjected to oscillation in a single linear dimension with a displacement of 1 mm or more and a frequency of 3 to 100 Hz during steps (ii) and (iii), said oscillation subjecting the tissue sample to a g-force of 6 to 50 ms$^{-2}$ thereby producing a decellularised tissue scaffold.

2. The method according to claim 1 wherein the tissue sample is subjected to oscillation at 3 to 75 Hz.

3. A method according to claim 1 wherein the oscillation has a displacement of 5 to 50 mm.

4. The method according to claim 1 wherein the osmotic agent is a hypotonic agent.

5. The method according to claim 4 wherein the hypotonic agent is deionised water.

6. The method according to claim 1 wherein the detergent comprises polyethylene glycol p-(1,1,3,3-tetramethylbutyl)-phenyl ether.

7. The method according to claim 1 wherein the detergent comprises sodium dodecyl sulfate (SDS).

8. The method according to claim 1 wherein the detergent comprises sodium deoxycholate (SdC).

9. The method according to claim 1 wherein the tissue sample is further treated with the detergent in combination with a protease.

10. The method according to claim 9 wherein the protease is trypsin.

11. The method according to claim 1 wherein the cells in the tissue sample are mechanically damaged in step (i).

12. The method according to claim 11 wherein the cells are mechanically damage by freezing and thawing the tissue sample.

13. The method according to claim 1 comprising;
(a) exposing the tissue sample obtained from step (i) to deionised water,
(b) repeating step (a),
(c) exposing the tissue sample obtained from step (c) to detergent and protease,
(d) re-exposing the tissue sample obtained from step (c) to detergent and protease,
(e) repeating step (d) 0 to 10 times,
(f) exposing the tissue sample obtained from step (e) to saline,
(g) repeating step (f) 0-10 times,
(h) repeating steps (a) to (e) 0-10 times,
(i) exposing the tissue sample obtained from step (h) to saline, and
(j) repeating step (i) 0-10 times.

14. The method according to claim 1 comprising;
(a) exposing the tissue sample obtained from step (i) to deionised water,
(b) repeating step (a) 4 times,
(c) exposing the tissue sample obtained from step (b) to detergent and protease for 2 minutes,
(d) re-exposing the tissue sample obtained from step (c) to detergent and protease for 4 minutes,
(e) repeating step (d),
(f) exposing the tissue sample obtained from step (e) to saline,
(g) repeating step (f) 4 times,
(h) repeating steps (a) to (e),
(i) exposing the tissue sample obtained from step (h) to saline, and
(j) repeating step (i) 2 times.

15. A method according to claim 1 comprising;
(a) exposing the tissue sample obtained from step (i) to deionised water,
(b) repeating step (a) 10 times,
(c) exposing the tissue sample obtained from step (b) to detergent and protease for 2 minutes,
(d) re-exposing the tissue sample obtained from step (c) to detergent and protease for 4 minutes,
(e) repeating step (d),
(f) exposing the tissue sample obtained from step (e) to saline,
(g) repeating step (f) 4 times,
(h) repeating steps (a) to (e),
(i) exposing the tissue sample obtained from step (h) to saline, and
(j) repeating step (i) 2 times.

16. A method according to claims 1 comprising;
(a) exposing the tissue sample obtained from step (i) to deionised water,
(b) repeating step (a) 11 times,
(c) exposing the tissue sample obtained from step (b) to detergent and protease for 2 minutes,
(d) re-exposing the tissue sample obtained from step (c) to detergent and protease for 4 minutes,
(e) repeating step (d),
(f) exposing the tissue sample obtained from step (e) to saline for 2 minutes,
(g) re-exposing the tissue sample obtained from step (f) to saline for 5 minutes, and
(h) repeating step (g) 2 times.

17. The method according to claim 13 wherein the tissue sample is a liver sample.

18. The method according to claim 1 comprising;
(a) exposing the tissue sample obtained from step (i) to deionised water,
(b) repeating step (a) 5 to 10 times,
(c) exposing the tissue sample obtained from step (b) to detergent,
(d) repeating step (a) 5 to 10 times with the tissue sample obtained from step (c),
(e) exposing the tissue sample obtained from step (d) to saline, and
(f) optionally repeating steps (a) to (e) one or more times.

19. The method according to claim 18 wherein the tissue sample is a kidney or heart sample.

20. The method according to claim 13 wherein the tissue sample is oscillated vertically at 50 Hz.

21. The method according to claim 1 comprising;
(a) exposing the tissue sample obtained from step (i) to deionised water,
(b) repeating step (a) 19 times,
(c) exposing the tissue sample obtained from step (b) to detergent and protease for 2 minutes,
(d) re-exposing the tissue sample obtained from step (c) to detergent and protease for 2 minutes,
(e) repeating step (d),
(f) exposing the tissue sample obtained from step (e) to saline
(g) repeating step (f) 4 times,
(h) repeating steps (a) to (e) 2 times,
(i) exposing the tissue sample obtained from step (h) to saline, and
(j) repeating step (i) 2 times.

22. The method according to claim 1 comprising;
(a) exposing the tissue sample obtained from step (i) to deionised water,
(b) repeating step (a) 9 times,
(c) exposing the tissue sample obtained from step (b) to detergent and protease for 2 minutes,
(d) re-exposing the tissue sample obtained from step (c) to detergent and protease for 4 minutes,
(e) repeating step (d)
(f) repeating steps (c) to (e),
(g) exposing the tissue sample obtained from step (f) to saline, and
(h) repeating step (g) 2 times.

23. The method according to claim 1 comprising;
(a) exposing the tissue sample obtained from step (i) to deionised water,
(b) repeating step (a) 10 times,
(c) exposing the tissue sample obtained from step (b) to detergent and protease for 2 minutes, (d) re-exposing the tissue sample obtained from step (c) to detergent and protease for 4 minutes,
(e) repeating step (d),
(f) exposing the tissue sample obtained from step (e) to saline, and
(g) repeating step (f) 2 times.

24. The method according to claim 1 comprising;
(a) exposing the tissue sample obtained from step (i) to deionised water
(b) repeating step (a) 20 times,
(c) exposing the tissue sample obtained from step (b) to detergent and protease for 2 minutes,
(d) re-exposing the tissue sample obtained from step (c) to detergent and protease for 4 minutes,
(e) repeating step (d),
(f) exposing the tissue sample obtained from step (e) to saline,
(g) repeating step (f) 5 times,
(h) repeating steps (a) to (d) 5 times,
(i) exposing the tissue sample obtained from step (h) to saline, and
(j) repeating step (i) 2 times.

25. The method according to claim 1 comprising;
(a) exposing the tissue sample obtained from step (i) to deionised water,
(b) repeating step (a) 4 times,
(c) exposing the tissue sample obtained from step (b) to detergent and protease for 2 minutes,
(d) re-exposing the tissue sample obtained from step (c) to detergent and protease for 4 minutes,
(e) repeating step (d),
(f) exposing the tissue sample obtained from step (e) to peracetic acid (PAA),
(g) repeating step (f) once,
(h) exposing the tissue sample obtained from step (g) to ammonium hydroxide ($NH_4OH$),
(i) repeating step (h) 2 times,
(j) exposing the tissue sample obtained from step (i) to deionised water,
(k) repeating step (j) 10 times,
(l) repeating steps (c) and (d) with the tissue sample obtained from step (k),
(m) exposing the tissue sample obtained from step (l) to saline, and
(n) repeating step (m) 2 times.

26. The method according to claim 21 wherein the tissue sample is a liver, pancreas or intestine sample.

27. The method according to claim 21 wherein the tissue sample is oscillated horizontally at 30 Hz.

28. The method according to claim 1 wherein the tissue sample is exposed to the osmotic agent and/or the detergent for 2 to 4 minutes in each repetition of steps (ii) and (iii).

29. The method according to claim 1 further comprising sterilising the tissue scaffold following decellularisation.

30. The method according to claim 1 further comprising repopulating the decellularised tissue scaffold with cells to produce a recellularised tissue scaffold.

31. A method for testing a compound, drug, biological agent, device or therapeutic intervention, comprising:
providing a sample of the decellularised tissue scaffold produced according to the method of claim 1, optionally repopulating the decellularised tissue sample with cells to produce a recellularised tissue,
contacting the decellularised tissue sample or the recellularised tissue with a compound, drug, biological agent, device or therapeutic intervention, and
measuring the effect of the compound, drug, biological agent, device or therapeutic intervention on the decellularised tissue sample or the recellularised tissue.

32. A method for identifying one or more extracellular matrix biomarkers, comprising:
providing a sample of the decellularised tissue scaffold produced according to the method of claim 1,
contacting the decellularised tissue sample to a protease that degrades one or more extracellular matrix components,
measuring degradation of the one or more components of the decellularised tissue sample by the protease, and
identifying said one or more components degraded by the protease as extracellular matrix biomarkers.

* * * * *